(12) United States Patent
Park

(10) Patent No.: US 11,432,866 B2
(45) Date of Patent: Sep. 6, 2022

(54) ELECTROSURGERY SMOKE SUCTION APPARATUS

(71) Applicant: Ik Ro Park, Irvine, CA (US)

(72) Inventor: Ik Ro Park, Irvine, CA (US)

( * ) Notice: Subject to any disclaimer, the term of this patent is extended or adjusted under 35 U.S.C. 154(b) by 674 days.

(21) Appl. No.: 16/266,871

(22) Filed: Feb. 4, 2019

(65) Prior Publication Data

US 2020/0246057 A1 Aug. 6, 2020

(51) Int. Cl.
*A61B 18/14* (2006.01)
*A61B 18/12* (2006.01)
*A61B 18/00* (2006.01)

(52) U.S. Cl.
CPC ...... *A61B 18/1402* (2013.01); *A61B 18/1206* (2013.01); *A61B 18/14* (2013.01); *A61B 18/148* (2013.01); *A61B 2018/00178* (2013.01); *A61B 2018/00196* (2013.01); *A61B 2018/00589* (2013.01); *A61B 2018/00601* (2013.01); *A61B 2018/00607* (2013.01); *A61B 2018/00702* (2013.01); *A61B 2018/128* (2013.01); *A61B 2018/1412* (2013.01); *A61B 2218/008* (2013.01)

(58) Field of Classification Search
CPC ... A61B 18/148; A61B 18/14; A61B 18/1402; A61B 18/042; A61B 18/082; A61B 2018/00958; A61B 2018/00196; A61B 2018/1412; A61B 2018/00916; A61B 2018/00946; A61B 2018/00702; A61B 2018/00589; A61B 2018/00601; A61B 2018/00607; A61B 2018/1472; A61B 2018/1475; A61B 2018/122; A61B 2218/008; A61B 2218/002; A61B 2218/007

USPC ............ 606/41, 42, 45, 49; 607/98, 99, 101, 607/104, 105, 107, 115, 116
See application file for complete search history.

(56) References Cited

U.S. PATENT DOCUMENTS

| | | | | |
|---|---|---|---|---|
| 4,528,983 A * | 7/1985 | Erb | ......................... | A61B 17/36 128/303.1 |
| 5,154,709 A * | 10/1992 | Johnson | .................. | A61B 17/39 606/45 |
| 5,607,449 A * | 3/1997 | Tontarra | .................. | A61B 17/28 606/205 |
| 5,857,997 A * | 1/1999 | Cimino et al. | ........ | A61M 37/00 604/95 |
| 8,518,018 B2 * | 8/2013 | Minskoff | ........... | A61B 18/1402 606/27 |

(Continued)

FOREIGN PATENT DOCUMENTS

| KR | 2020110002463 | | 3/2011 |
|---|---|---|---|
| WO | WO2017/099291 | A1 * | 6/2017 |

*Primary Examiner* — Thomas A Giuliani
(74) *Attorney, Agent, or Firm* — Studebaker & Brackett PC

(57) ABSTRACT

An electrosurgical apparatus comprises: a main body formed with a suction passage therein; an extension member including a length adjusting tube coupled to a side of the main body and formed therein with an induction passage communicating with the suction passage, and a sliding part configured to slide while being guided by the length adjusting tube; and a blade configured such that a first end thereof protrudes outside through the sliding part, and a second end thereof extends to be electrically connected to the main body and receives high frequencies from the main body, wherein an entire length of the extension member is adjusted according to a position of the sliding part sliding along the length adjusting tube.

23 Claims, 16 Drawing Sheets

(56) References Cited

U.S. PATENT DOCUMENTS

| | | | |
|---|---|---|---|
| 2003/0018332 A1* | 1/2003 | Schmaltz et al. | A61B 18/18 606/51 |
| 2005/0065541 A1* | 3/2005 | Abidin et al. | A61B 17/32 606/167 |
| 2009/0062791 A1* | 3/2009 | Lee | A61B 18/1402 606/45 |
| 2011/0190768 A1* | 8/2011 | Shvetsov et al. | A81B 18/18 606/48 |
| 2013/0131705 A1* | 5/2013 | Akagane | A61N 7/00 606/169 |
| 2014/0052131 A1* | 2/2014 | Busch-Madsen et al. | A61B 18/14 |
| 2015/0257816 A1* | 9/2015 | Ineson | A61B 18/1402 606/49 |
| 2016/0213422 A1* | 7/2016 | Ineson | A61B 18/14 |
| 2018/0243026 A1* | 8/2018 | Park | A61B 18/14 |

* cited by examiner

ELECTROSURGERY SMOKE SUCTION APPARATUS

BACKGROUND

The present invention relates generally to an electrosurgical apparatus. More particularly, the present invention relates to an electrosurgical apparatus, in which the smoke generated in the body tissue in contact with a blade is easily collected toward a main body.

In general, an electrosurgical unit (ESU) is a typical medical device that is used to cut a part of human tissue or coagulate tissues and blood using electricity instead of surgical knife, mainly in a surgical operation. The ESU, which utilizes the principle of generating short sparks or heat without causing electric shock or stimulation to the muscles when a high frequency current flows through the human body, is used to cut the desired tissue with a high frequency energy of about 100° C. or coagulate the same with a high frequency energy of about 60° C.

Meanwhile, the ESU cuts or coagulates using the principle of high frequency current, and in this process, due to the high temperature of the electrode, moisture in the tissue is evaporated and smoke is generated. There are substances in the smoke that can adversely affect the health of a doctor who performs the operation. If the operation is carried out for a long time, the doctor and the nurse may inhale a large amount of smoke, which can seriously harm physical health. Thus, it is important that a doctor does not inhale such smoke during the surgical procedure. Further, smoke may blur the doctor's vision.

FIG. 1 is a view showing a conventional electrosurgical apparatus with suction ability.

Referring to FIG. 1, a conventional electrosurgical apparatus 10 with suction ability is configured such that a suction passage part 14 is mounted to a lower portion of a main body 12. Further, a blade 16 is mounted to an end of the main body 12 to receive high frequencies from the main body 12.

In the conventional electrosurgical apparatus 10, when a practitioner cuts or coagulates the body tissue using the blade 16 while gripping the main body 12, smoke is generated in the body tissue in contact with the blade 16. Generally, since the smoke heated by combustion is hotter than the ambient air, the density thereof is low and it rises vertically.

However, when gripping the main body 12, the practitioner grips the main body 12 at a slant angle of about 45 degrees, just as he or she would hold a normal pen, so the smoke generated around the blade 16 is not guided to the suction passage part 14 but rises vertically as described above since the distance between main body 12 and the blade 16 is too far, and accordingly the smoke is not properly sucked in through the suction passage part 14.

The foregoing is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problems occurring in the related art, and the present invention is intended to propose an electrosurgical apparatus, in which the smoke generated in the body tissue in contact with a blade is easily collected toward a main body.

In order to achieve the above object, according to some aspect of the present invention, there is provided an electrosurgical apparatus including: a main body formed with a suction passage therein; an extension member including a length adjusting tube coupled to a side of the main body and formed therein with an induction passage communicating with the suction passage, and a sliding part configured to slide while being guided by the length adjusting tube; and a blade configured such that a first end thereof protrudes outside through the sliding part, and a second end thereof extends to be electrically connected to the main body and receives high frequencies from the main body, wherein an entire length of the extension member is adjusted according to a position of the sliding part sliding along the length adjusting tube.

Further, the length adjusting tube may include a length adjusting part formed in a tubular shape and formed with the induction passage therein, a coupling part protruding from a rear end of the length adjusting part facing the main body so as to be coupled with the main body, and a length adjusting-locking step protruding from an outer circumferential surface of a front end of the length adjusting part disposed opposite to the main body; and the sliding part may be formed in a tubular shape having an inner circumferential diameter larger than an outer circumferential diameter of the length adjusting-locking step, wherein the sliding part includes a stopper having elasticity protruding inwardly from a rear end thereof facing the main body, and in a process of inserting the front end of the length adjusting part into the rear end of the sliding part, the stopper is elastically deformed by pressure of the length adjusting-locking step when the length adjusting-locking step passes by the stopper.

Further, the length adjusting part may be provided with a guide groove concavely formed from the front end towards the rear end thereof; and after the front end of the length adjusting part may be inserted into the rear end of the sliding part, when the sliding part is moved along the length adjusting part, the stopper slides along the guide groove.

Further, the sliding part may be provided with at least one through-hole at the rear end thereof, and the stopper may include: a ring-shaped fitting part fitted over an outer circumferential surface of the rear end of the sliding part; and a stop protrusion protruding from the fitting part toward inside the sliding part via the through-hole.

Further, the stop protrusion may be provided with a pair of latching portions protruding from opposite sides of a front end portion thereof, and when the front end portion of the stop protrusion is inserted into the through-hole, the pair of latching portions may be elastically deformed and engaged with an inner side of the sliding part.

Further, the length adjusting-locking step may be provided with a fitting groove to allow an O-ring to be fitted over the outer circumferential surface thereof, and an outer circumferential surface of the O-ring may be brought in close contact with an inner circumferential surface of the sliding part.

Further, in a state where the rear end of the sliding part being moved along the length adjusting part is positioned to be in contact with the coupling part, the sliding part may be integrally provided at a front end thereof with an induction extension part protruding forwardly more than the front end of the length adjusting part; the induction extension part may be configured to have a diameter smaller than a diameter of the sliding part; and the blade may protrude outside the induction extension part via the sliding part.

Further, the main body may include: an outer body extending in a longitudinal direction, and being formed therein with a space along the longitudinal direction; and an inner body configured to be slidable along the space, and provided therein with the suction passage along the longitudinal direction, wherein the length adjusting tube is coupled to the inner body.

According to some aspect of the present invention, there is further provided an electrosurgical apparatus including: a main body formed with a suction passage therein; an extension member including an extension tube coupled to a side of the main body and formed therein with an induction passage communicating with the suction passage, and a sliding tube configured to slide along the extension tube while being inserted in the extension tube; and a blade configured such that a first side thereof protrudes outside through the sliding tube and a second side thereof is electrically connected to the main body to receive high frequencies from the main body, wherein an entire length of the extension member is adjusted according to a position of the sliding tube sliding along the extension tube, and an open front end of the sliding tube is configured to protrude to be gradually away from the main body from a bottom to a top thereof.

Further, the extension tube may include: a sliding guide part formed in a tubular shape; an insertion guide part formed integrally protruding from a rear end of the sliding guide part facing the main body to be coupled to the main body; the induction passage formed through the sliding tube and the insertion guide part; and a coupling part configured to allow the blade to be coupled to the sliding guide part or the insertion guide part, and the sliding tube may include: an insertion part configured to slide while being inserted into the sliding guide part; and a grip part integrally provided at a front end of the insertion part, wherein an open front end of the grip part is provided with a suction guider configured to protrude to be gradually away from the main body from a bottom to a top thereof.

Further, an upper portion of the suction guider may be formed to be inclined downward to be close to the blade.

Further, the grip part may be formed to have an outer circumferential diameter larger than an outer circumferential diameter of the insertion part.

Further, the sliding guide part may be provided an inner circumferential surface thereof with a guide rail concavely formed along a longitudinal direction of the sliding guide part, with the guide rail provided with a through-coupling portion at an end thereof disposed opposite to the main body to be exposed to an outside, the insertion part may be provided an outer circumferential surface thereof with a guide protrusion to slide along the guide rail, and when the insertion part is inserted into the sliding guide part, the guide protrusion may be inserted into the guide rail through the through-coupling portion.

Further, a stopper may be detachably coupled to the through-coupling portion, with a blocking protrusion formed protruding from an inner side of the stopper; when the stopper is detached from the through-coupling portion, the end of the guide rail may be exposed to the outside, such that the guide protrusion is inserted into the guide rail; and when the stopper is coupled to the through-coupling portion in a state where the guide protrusion is inserted into the guide rail, the end of the guide rail may be blocked from the outside by the blocking protrusion, such that the guide protrusion being moved along the guide rail is stopped by the blocking protrusion.

Further, the blocking protrusion may protrude from a middle portion of the stopper.

Further, the insertion part may be provided with a flat portion at a position of the outer circumferential surface thereof facing the guide rail; and when the insertion part is moved along the sliding guide part, the flat portion may slide in contact with the blocking protrusion.

Further, the stopper may be provided with elastic engaging hooks on opposite sides thereof, and the through-coupling portion may be provided with engaging grooves on opposite sides thereof to be engaged with the engaging hooks when the stopper is coupled through the through-coupling portion.

Further, the insertion part may be provided with hook guide channels formed to be concave at positions of opposite sides thereof brought in contact with the engaging hooks such that the engaging hooks slide while being guided thereby.

Further, the main body may include: an outer body formed with a space therein; and an inner body configured to be slidable along the space, and provided with the suction passage therein, wherein the extension tube is coupled to the inner body.

Further, the extension tube may be provided with a support protrusion at a lower side portion thereof to support a lower portion of the sliding tube.

Further, a friction part may be provided between the extension tube and the sliding tube; and a first side of the friction part may be brought into close contact with the sliding tube, and a second side of the friction part may be brought into close contact with the extension tube.

Further, the sliding tube may be provided with a friction guide groove formed to be concave to guide the friction part.

According to some aspect of the present invention, there is further provided an electrosurgical apparatus including: a main body formed with a suction passage therein; an extension member including an extension guide tube coupled to a side of the main body and formed therein with an induction passage communicating with the suction passage, a sliding part configured to slide along the extension guide tube, and a suction guider coupled to a front end of the sliding part that does not face the main body; and a blade locked to an inside of the extension guide tube, and configured such that a first side thereof protrudes outside through the suction guider and a second side thereof is connected to the main body to receive high frequencies from the main body, wherein an open rear end of the suction guider is coupled to the front end of the sliding part, and an open front end of the suction guider is configured to protrude to be gradually away from the main body from a bottom to a top thereof.

Further, the extension guide tube may include an extension part formed in a tubular shape with the induction passage formed therein, a coupling part protruding from a rear end of the extension part facing the main body so as to be coupled with the main body, and an extension-locking step protruding from an outer circumferential surface of a front end of the extension part disposed opposite to the main body; the sliding part may be formed in a tubular shape having an inner circumferential diameter larger than an outer circumferential diameter of the extension-locking step, and may include a sliding-locking step protruding toward an outer circumferential surface of the extension part along an inner circumferential surface of a rear end of the sliding part disposed at a position facing the main body; and an open front end of the sliding part may be disposed at the extension part via the coupling part, wherein when the front end of the sliding part is disposed to protrude forwardly more than the extension part, the suction guider is coupled to the front end of the sliding part.

Further, the suction guider may be configured to have an inner circumference smaller than an outer circumference of the extension-locking step; when the rear end of the sliding part is disposed at the extension-locking step while the sliding part is slidably moved forwardly along the extension part, the sliding-locking step is engaged with the extension-locking step to limit forward movement of the sliding part; and when the suction guider coupled to the front end of the sliding part is disposed at the extension-locking step while the sliding part is slidably moved backwardly along the extension part, the suction guider is engaged with the extension-locking step to limit backward movement of the sliding part.

Further, the extension part may be protrudingly provided with at least one guide rail on an outer side thereof along a longitudinal direction, the sliding-locking step may be concavely provided with a guide groove to allow the guide rail to be inserted thereinto, and the guide groove may be moved along the guide rail when the sliding part slides.

Further, the guide groove and the guide rail may be brought in contact with each other, and the guide groove may be moved along the guide rail by external pressure.

Further, the suction guider may include an inlet coupling part coupled to the front end of the sliding part, and a suction induction part integrally protruding from a front side of the inlet coupling part to be away from the main body; and the suction induction part may be configured to protrude to be gradually away from the main body from a lower portion to an upper portion thereof, wherein the upper portion of the suction induction part protrudes to be inclined so as to be close to the blade.

Further, the suction guider may include an inlet coupling part coupled to the front end of the sliding part, and a suction induction part integrally protruding from a front side of the inlet coupling part to be away from the main body; and the suction induction part may be configured to protrude to be gradually away from the main body from a lower portion to an upper portion thereof, wherein the suction induction part is provided at a lower end thereof with an inclined portion to be inclined.

Further, the main body may include: an outer body extending in a longitudinal direction, and being formed therein with a space along the longitudinal direction; and an inner body configured to be slidable along the space, and provided therein with the suction passage along the longitudinal direction, wherein the extension guide tube is coupled to the inner body.

According to the present invention, it is advantageous in that since the sliding part is configured to be moved along the length adjusting part, when the sliding part is moved forward, a small portion of the blade is exposed outside the induction extension part, so the end of the blade 700 and the induction extension part are positioned to be close to each other, and accordingly, the smoke generated in the body in contact with the blade is easily collected to the inside of the induction extension part.

It is further advantageous in that since the stopper is mounted to the sliding part, the forward movement of the sliding part being moved along the length adjusting part is limited, whereby the sliding part is not undesirably separated from the length adjusting part.

It is further advantageous in that when the sliding part is moved along the length adjusting part, the stop protrusion of the stopper slides along the guide groove, whereby the sliding part cannot be undesirably rotated, and thus, when a user arbitrarily moves the sliding part while gripping the sliding part, it is possible to stably move the sliding part.

It is further advantageous in that since the O-ring is fitted over the length adjusting-locking step, and the outer circumferential surface of the O-ring is brought in close contact with the inner circumferential surface of the sliding part, it is possible to prevent the sliding part inserted in the length adjusting part from being undesirably moved.

It is further advantageous in that since the upper portion of the suction guider is formed to protrude more toward the end of the blade than the lower portion of the suction guider, the smoke generated in the body tissue in contact with the end of the blade is easily collected to the upper portion of the suction guider.

It is further advantageous in that since the sliding tube slides along the extension tube, it is possible to easily adjust the entire length of the extension member. Further, when the sliding tube slides to be away from the main body, the distance between the suction guider and the front end of the blade becomes shorter, whereby a large amount of smoke generated in the blade is easily collected into the suction guider.

It is further advantageous in that since the guide protrusion of the insertion part slides along the guide rail, the upper portion and the lower portion of the suction guider are not undesirably inverted, whereby the upper portion of the suction guider always protrudes more toward the end of the blade.

It is further advantageous in that when the stopper is coupled to the through-coupling portion in the state where the guide protrusion is inserted into the guide rail, the guide protrusion being moved along the guide rail is stopped by the blocking protrusion, whereby with a simple structure, the insertion part inserted into the sliding guide part cannot be undesirably separated from sliding guide part.

It is further advantageous in that since a frictional force is generated between the flat portion and the blocking protrusion, the insertion part cannot be moved undesirably, whereby when the practitioner forcibly moves the insertion part forward or backward while gripping the grip part, the insertion part is maintained at the moved position.

It is further advantageous in that since the blocking protrusion is formed to have a large area, even though the practitioner moves the sliding tube forward with more force than necessary, the guide protrusion cannot pass over the blocking protrusion, and thus, the blocking protrusion firmly supports the sliding tube being inserted into the extension tube.

It is further advantageous in that since the support protrusion firmly supports the lower portion of the sliding tube, even if the sliding tube is moved forward, the sliding tube is not shaken up and down undesirably.

It is further advantageous in that since the friction part is provided between the sliding tube and the extension tube, the sliding tube cannot be undesirably moved but can slide only when there is pressure by a user.

It is further advantageous in that since the suction guider is provided at the lower front end thereof with the inclined portion, the suction guider is easily moved along skin with the inclined portion being stably brought in contact with the skin.

It is further advantageous in that since the sliding part of the extension member is configured to slide along the extension guide tube, when the sliding part is slidably moved forward, the suction guider is moved to be close to the end of the blade, and thus, the smoke generated in the body tissue in contact with the blade is easily collected to the inside of the suction guider.

It is further advantageous in that since the sliding part is slidably moved along the guide rail, the sliding part is not undesirably rotated within the extension part, whereby the upper portion and the lower portion of the suction guider connected with the sliding part are not undesirably inverted.

It is further advantageous in that since the sliding-locking step is configured to be engaged with the extension-locking step when the sliding part is slidably moved forward along the extension part, and thus, the sliding part being moved forward is not undesirably separated from the extension part.

It is further advantageous in that when the practitioner forcibly moves the sliding part forward or backward while holding the sliding part, the sliding part is maintained at a position moved by the practitioner.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, an electrosurgical apparatus according to exemplary embodiments of the present invention will be described in detail with reference to the accompanying drawings.

Figure 1:
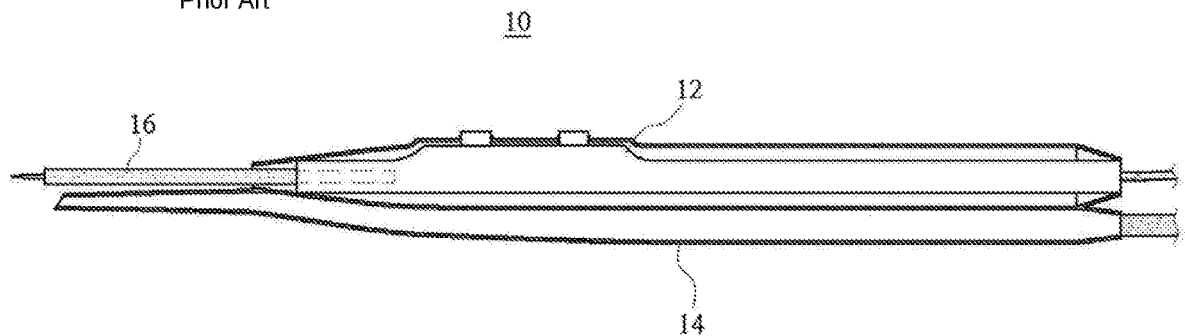
FIG. 1 is a view showing a conventional electrosurgical apparatus with suction ability.
Figure 2:
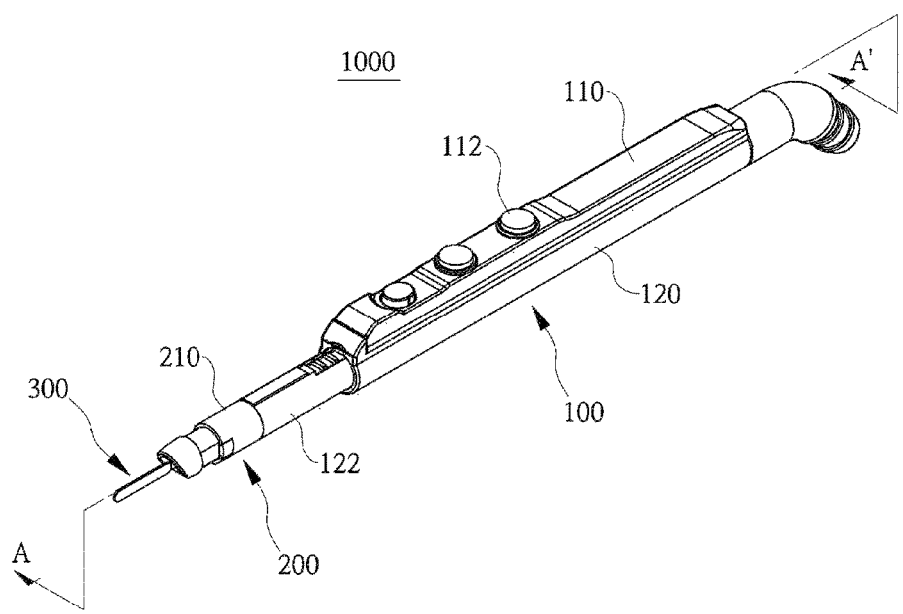
FIG. 2 is a schematic view showing an electrosurgical apparatus according to a first preferred embodiment of the present invention.
Figure 3:
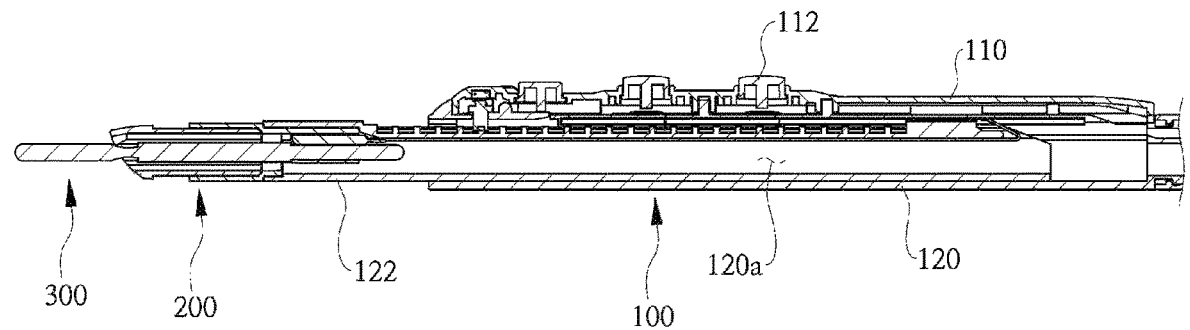
FIG. 3 is a schematic sectional view taken along line A-A' of the electrosurgical apparatus according to the first preferred embodiment of the present invention.

FIG. 2 is a schematic view showing an electrosurgical apparatus according to a first preferred embodiment of the present invention; and FIG. 3 is a schematic sectional view taken along line A-A' of the electrosurgical apparatus according to the first preferred embodiment of the present invention.

Referring to FIGS. 2 and 3, an electrosurgical apparatus 1000 according to the first preferred embodiment of the present invention is used by a practitioner such as a physician to cut or coagulate a part of a patient's body tissue, and includes a main body 100, an extension member 200, and a blade 300.

The main body 100 includes an outer body 110, and an inner body 120. The outer body 110 is formed in a long shape along the longitudinal direction so that the practitioner can grasp the same by hand, and a space (not shown) is formed therein along the longitudinal direction. Further, an operation button 112 is provided on the upper portion of the outer body 110, and a substrate (not shown) connected to the operation button 112 is provided inside the upper portion of the outer body 110. The substrate is configured to control the amount of high frequency energy transmitted from the outside by the operation of the operation button 112, and then transmit the adjusted amount to the blade 300. The current and voltage of high frequency may be varied depending on the patient's affected area and the surgical situation.

The inner body 120 is inserted into the lower portion of the outer body 110, and is formed in a long shape along the longitudinal direction, with a suction passage 120a formed therein along the longitudinal direction. The front of the suction passage 120a is coupled with the extension member 200, and the back thereof is connected with a separate suction means (not shown) provided outside to suck air, such that when the practitioner uses the blade 300 to cut or coagulate a part of the patient's body tissue, smoke spreading around the blade 300 is sucked in through the extension member 200 and the suction passage 120a. Further, an insertion guide protruding part 122 is formed protruding from the longitudinal front portion of the inner body 120 to allow the extension member 200 to be inserted therein. Meanwhile, although the main body 100 includes the outer body 110 and the inner body 120, this is only an embodiment of the present invention. In some cases, the outer body 110 and the inner body 120 may be integrally formed.

The extension member 200 allows the entire length to be increased or decreased, thereby guiding a suction guider 225 (shown in FIG. 4), which will be described later, to be close to or away from the front end of the blade 300.

The blade 300 is used to cut or coagulate a part of the patient's body tissue using high frequencies during the surgical procedure, and is formed in a long shape along the longitudinal direction and is fastened to the extension member 200. Further, the blade 300 is disposed inside the extension member 200, with the front end thereof protruding outside through the suction guider 225, and the rear end thereof extending in the direction of the inner body 120. Here, the inner body 120 is provided therein with a contact guide (not shown) for connecting the substrate and the blade 300 to each other such that the blade 300 receives high frequencies from the main body 100.

Hereinafter, unless noted otherwise, the front, front side, or front end refers to the direction away from the main body 100, and the rear, rear side, or rear end refers to the direction close to the main body 100.

Figure 4:
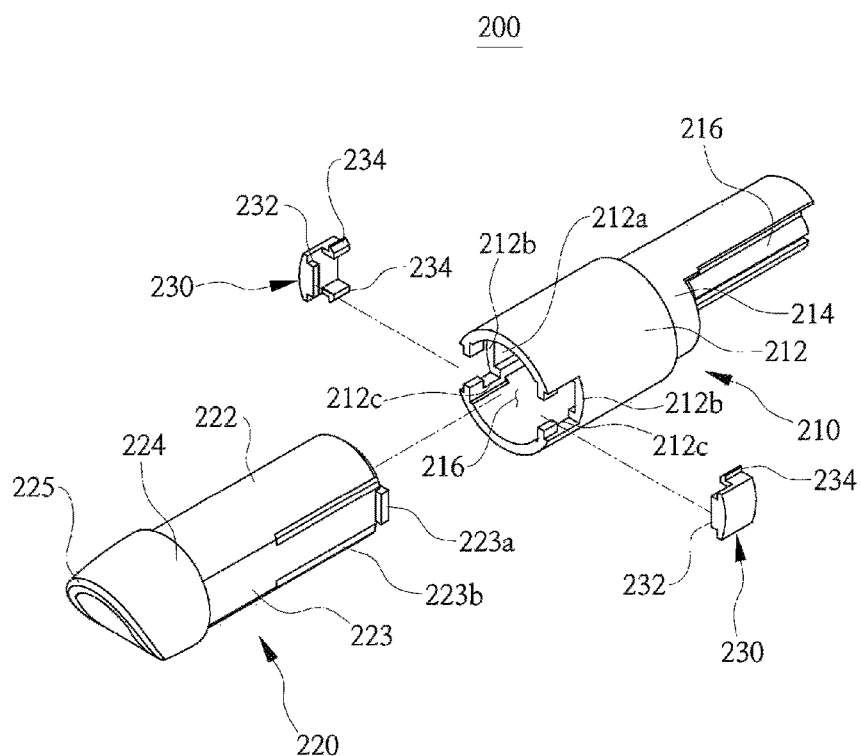
FIG. 4 is an exploded view showing an extension member of the electrosurgical apparatus according to the first preferred embodiment of the present invention.
Figure 5:
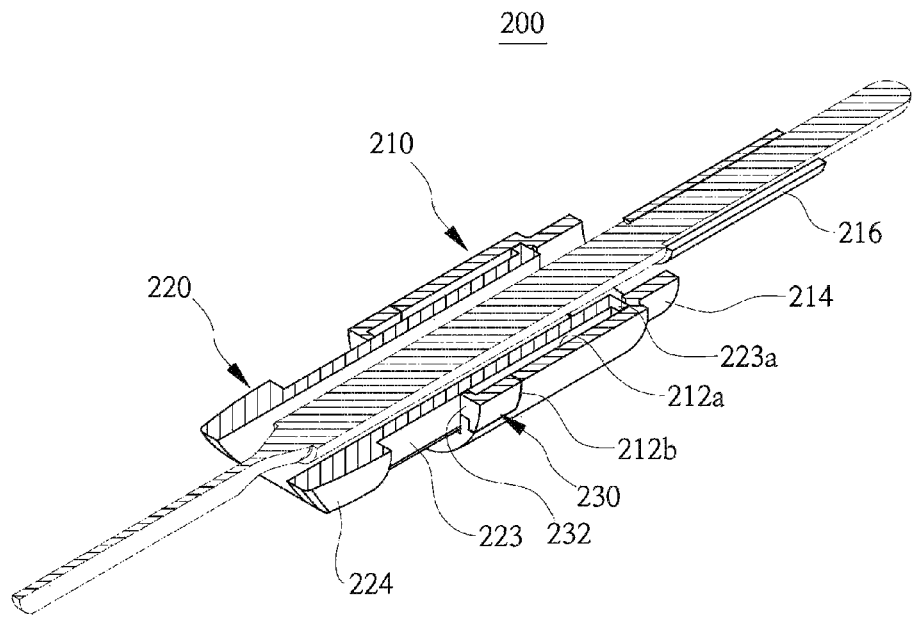
FIG. 5 is a schematic longitudinal sectional view showing the extension member of the electrosurgical apparatus according to the first preferred embodiment of the present invention.

FIG. 4 is an exploded view showing an extension member of the electrosurgical apparatus according to the first preferred embodiment of the present invention; FIG. 5 is a schematic longitudinal sectional view showing the extension member of the electrosurgical apparatus according to the first preferred embodiment of the present invention; and FIG. 6 is a schematic cross sectional view showing the extension member of the electrosurgical apparatus according to the first preferred embodiment of the present invention.

Figure 6:
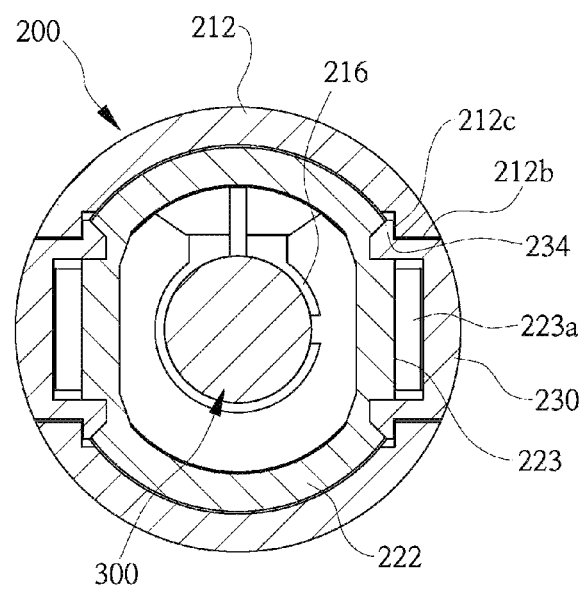
FIG. 6 is a schematic cross sectional view showing the extension member of the electrosurgical apparatus according to the first preferred embodiment of the present invention.

Referring to FIGS. 4 to 6, the extension member 200 includes an extension tube 210, a sliding tube 220, and a stopper 230. The extension tube 210 includes: a sliding guide part 212 formed in a tubular shape like a cylinder; and an insertion guide part 214 formed integrally protruding from a rear end of the sliding guide part 212 facing the main body 100 to be inserted into the insertion guide protruding part 122 of the main body 100. Further, a hollow induction passage 216 is formed through the sliding tube 220 and the insertion guide part 214. When the insertion guide part 214 is inserted into the insertion guide protruding part 122, the induction passage 216 and the suction passage 120a communicate with each other. Further, the sliding guide part 212 is provided an inner circumferential surface thereof with a guide rail 212a concavely formed along a longitudinal direction of the sliding guide part 212, wherein a through-coupling portion 212b is formed through an end of the guide rail 212a disposed opposite to the main body 100 to be exposed to the outside. The through-coupling portion 212b is formed to have an open front end such that a guide protrusion 223a to be described later is guided thereby. Further, a coupling part is provided such that the blade 300 is coupled to the sliding guide part 212 or the insertion guide part 214. The coupling part is, for example, formed protruding rearward from the upper portion of the rear end of the insertion guide part 214, wherein the coupling part is inserted into the insertion guide protruding part, and the rear end of the blade 300 is inserted into and coupled to the coupling part.

The sliding tube 220 includes: an insertion part 222 configured to slide while being inserted into the sliding guide part 212; and a grip part 224 integrally provided at a front end of the insertion part 222. The insertion part 222 is formed in a cylindrical shape having a length longer than the sliding guide part 212. The insertion part 222 is formed to have an outer circumferential diameter smaller than an inner circumferential diameter of the sliding guide part 212 to be inserted into the sliding guide part 212. Further, the outer circumferential diameter of the insertion part 222 is formed to be larger than the inner circumferential diameter of the insertion guide part 214, such that the insertion part 222 inserted into the sliding guide part 212 is stopped by the insertion guide part 214, whereby the rearward movement of the insertion part 222 is limited. Further, the insertion part 222 is provided with the guide protrusion 223a at the rear portion of the outer circumferential surface thereof to slide along the guide rail 212a while being inserted into the guide rail 212a. Herein, when the insertion part 222 is inserted into the sliding guide part 212, the guide protrusion 223a is inserted into the guide rail 212a through the open front end of the through-coupling portion 212b.

The grip part 224 is formed to have an outer circumferential diameter larger than the outer circumferential diameter of the insertion part 222. Thus, when the practitioner moves the grip part 224 back and forth while gripping the grip part 224, the grip part 224 can be easily moved with the nail or the finger of the practitioner hooked to the rear end of the grip part 224 connected with the insertion part 222. Further, an open front end of the grip part 224 is provided with the suction guider 225 configured to protrude to be gradually away from the main body 100 from a bottom to a top thereof. The upper portion of the suction guider 225 is formed to be inclined downward to be close to the blade 300.

Accordingly, with the practitioner gripping the main body 100 at an angle of 45 degrees, the upper portion of the suction guider 225 protrudes more toward the end of the blade 300 than the lower portion of the suction guider 225. Thus, the smoke generated in the body tissue in contact with the end of the blade 300 is easily collected to the upper portion of the suction guider 225. Meanwhile, as the guide protrusion 223a of the insertion part 222 slides along the guide rail 212a, the insertion part 222 cannot be rotated undesirably when being moved along the longitudinal direction of the sliding guide part 212, and accordingly, the suction guider 225 connected with the sliding guide part 212 cannot be rotated, whereby the upper portion and the lower portion of the suction guider 225 are not undesirably inverted so that the upper portion of the suction guider 225 always protrudes more toward the end of the blade 300.

The stopper 230 is configured to cover the through-coupling portion 212b, and is detachably coupled to the through-coupling portion 212b. To achieve this, a pair of elastic engaging hooks 234 are formed protruding on opposite sides of the stopper 230, and a pair of engaging grooves 212c are formed in opposite sides of the through-coupling portion 212b to be engaged with the engaging hooks 234. Further, when the stopper 230 is coupled to the through-coupling portion 212b, the pair of engaging hooks 234 are elastically deformed and detachably engaged with the engaging grooves 212c. Further, a blocking protrusion 232 is formed protruding from an inner side of the stopper 230, so as to limit the forward movement of the guide protrusion 223a being moved along the guide rail 212a. In other words, when the stopper 230 is detached from the through-coupling portion 212b, the end of the guide rail 212a is exposed to the outside by the through-coupling portion 212b, and in this state, the insertion part 222 is inserted into the sliding guide part 212. Here, the guide protrusion 223a is inserted into the guide rail 212a via the through-coupling portion 212b. Further, when the stopper 230 is coupled to the through-coupling portion 212b in the state where the guide protrusion 223a is inserted into the guide rail 212a, the end of the guide rail 212a is blocked from the outside by the blocking protrusion 232, such that the guide protrusion 223a being moved along the guide rail 212a is stopped by the blocking protrusion 232, and accordingly, the insertion part 222 inserted into the sliding guide part 212 cannot be undesirably separated from sliding guide part 212.

Meanwhile, at a position of the outer circumferential surface thereof facing the guide rail 212a, the insertion part 222 is provided with a flat portion 223 formed to be flat along the longitudinal direction of the insertion part 222. Further, when the insertion part 222 is moved along the sliding guide part 212, the flat portion 223 slides in contact with the blocking protrusion 232. As such, the blocking protrusion 232 is guided while being in surface contact with the flat portion 223, so that the insertion part 222 can stably slide along the blocking protrusion 232. Further, since a frictional force is generated between the flat portion 223 and the blocking protrusion 232, the insertion part 222 cannot be moved undesirably, and thus, when the practitioner forcibly moves the insertion part forward or backward while gripping the grip part 224, the insertion part 222 is maintained at the moved position.

Further, hook guide channels 223b are concavely formed in opposite sides of the flat portion 223 brought in contact with the engaging hooks 234 along the longitudinal direction, such that the engaging hooks 234 slide while being guided thereby. In other words, the hook guide channels 223b serve to provide a space to which the end portions of the engaging hooks 234 are accommodated.

Figure 7:
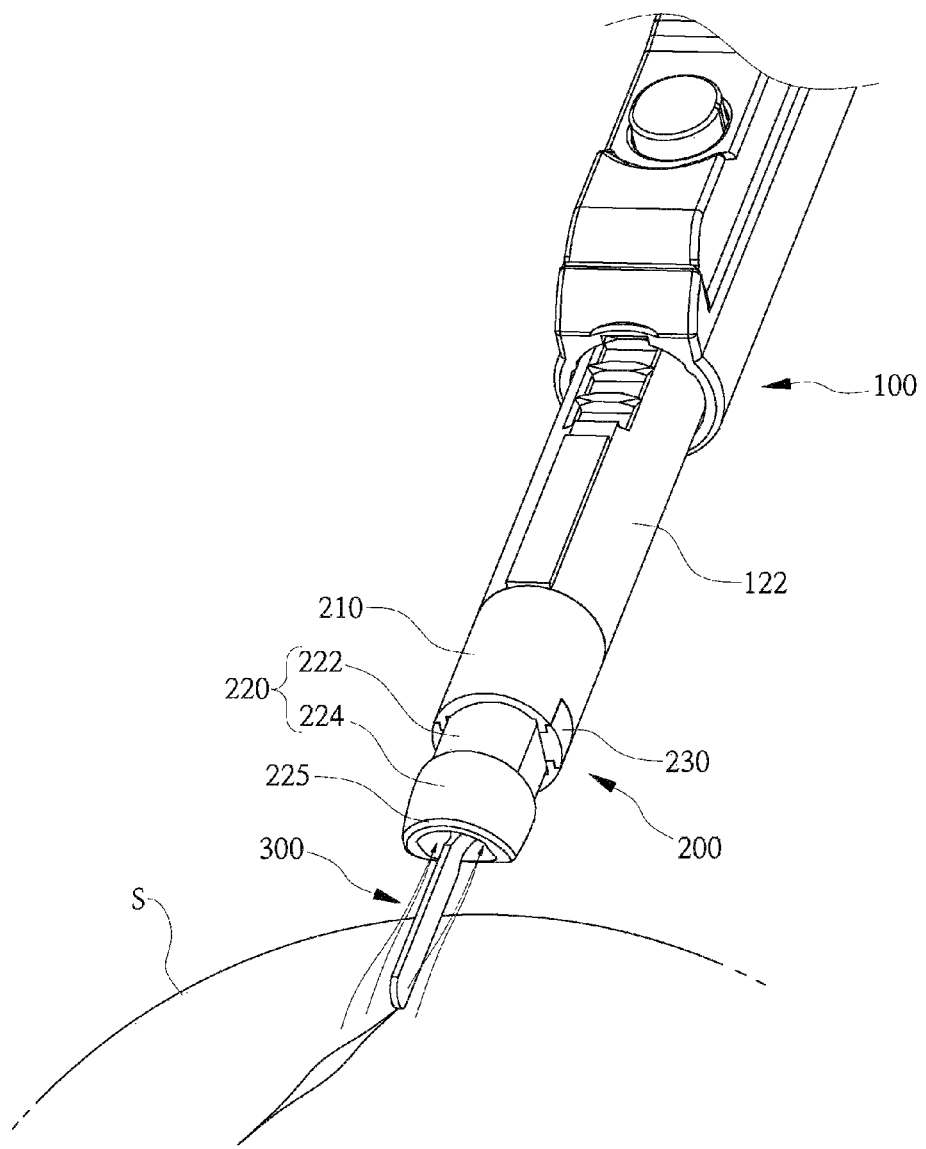
FIG. 7 is a view showing a state where smoke is collected through a suction guider of the electrosurgical apparatus according to the first preferred embodiment of the present invention.

FIG. 7 is a view showing a state where smoke is collected through a suction guider of the electrosurgical apparatus according to the first preferred embodiment of the present invention.

Referring to the drawing, with the practitioner gripping the main body 100 at an angle of 45 degrees, the upper portion of the suction guider 225 protrudes more toward the end of the blade 300 than the lower portion of the suction guider 225. Thus, the smoke generated in the body tissue S in contact with the end of the blade 300 is easily collected to the upper portion of the suction guider 225.

Figure 8:
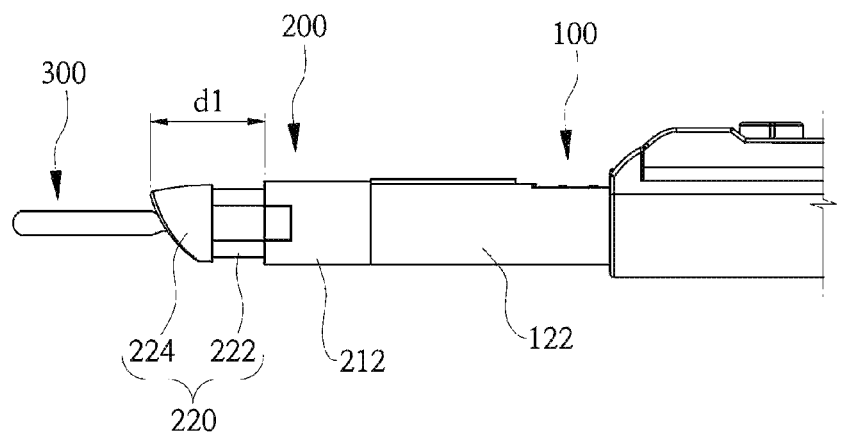
FIGS. 8 and 9 are schematic views showing length differences of an extension member depending on a position of a sliding tube of the electrosurgical apparatus according to the first preferred embodiment of the present invention.
Figure 9:
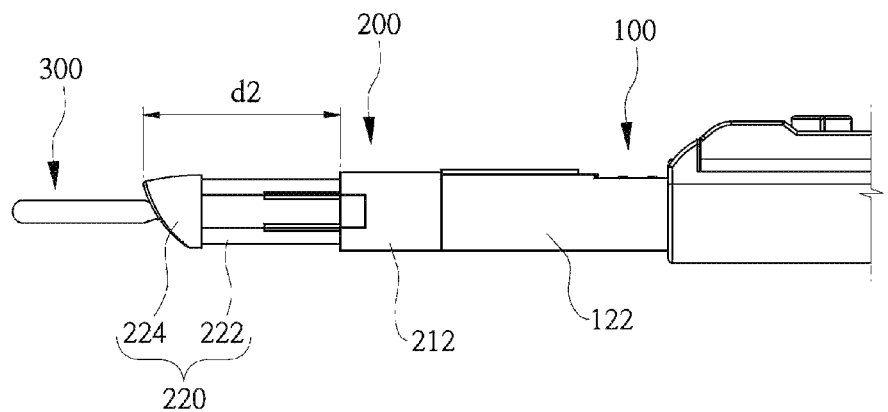

FIGS. 8 and 9 are schematic views showing length differences of an extension member depending on a position of a sliding tube of the electrosurgical apparatus according to the first preferred embodiment of the present invention.

Firstly, referring to FIG. 8, the practitioner moves the grip part 224 backward while gripping the grip part 224. Then, the insertion part 222 is moved backward, and the length of the sliding tube 220 exposed outside of the extension tube 210 is a first length d1. In this state, the distance between the suction guider 225 and the front end of the blade 300 becomes longer, and in some cases, if the smoke generated in the blade 300 is too much, the suction guider 225 may not perform a suction operation properly.

Next, referring to FIG. 9, the practitioner moves the grip part 224 forward while gripping the grip part 224. Then, the insertion part 222 is moved forward, and the length of the sliding tube 220 exposed outside of the extension tube 210 is a second length d2 longer than the first length d1. In this state, the distance between the suction guider 225 and the front end of the blade 300 becomes shorter, and thus, a large amount of smoke generated in the blade 300 is easily collected into the suction guider 225.

Figure 10:
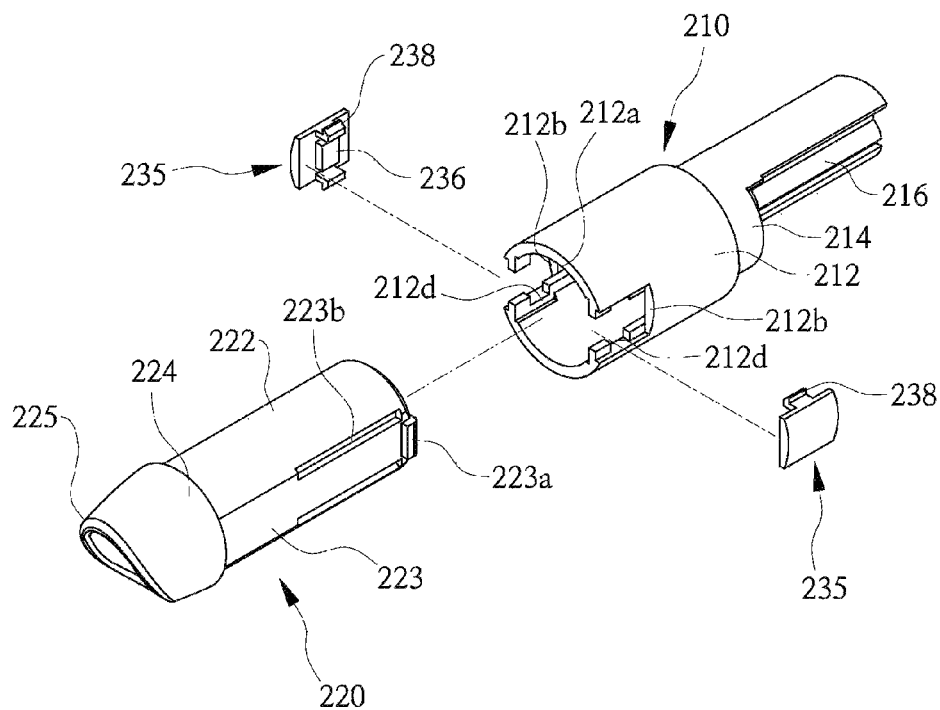
FIG. 10 is an exploded view showing the extension member of the electrosurgical apparatus according to a second preferred embodiment of the present invention.
Figure 11:
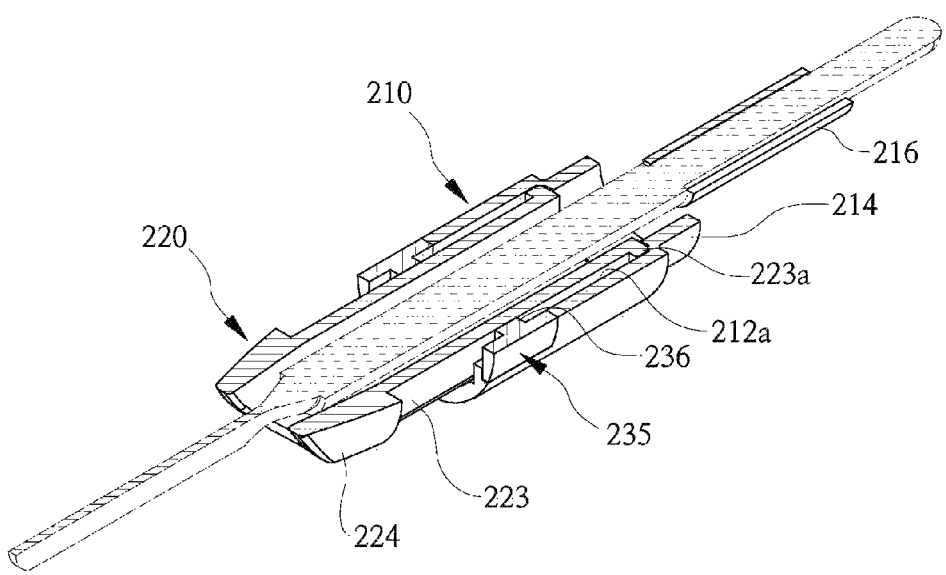
FIG. 11 is a schematic longitudinal sectional view showing the extension member of the electrosurgical apparatus according to the second preferred embodiment of the present invention.

FIG. 10 is an exploded view showing the extension member of the electrosurgical apparatus according to a second preferred embodiment of the present invention; FIG. 11 is a schematic longitudinal sectional view showing the extension member of the electrosurgical apparatus according to the second preferred embodiment of the present invention; and FIG. 12 is a schematic cross sectional view showing the extension member of the electrosurgical apparatus according to the second preferred embodiment of the present invention.

Figure 12:
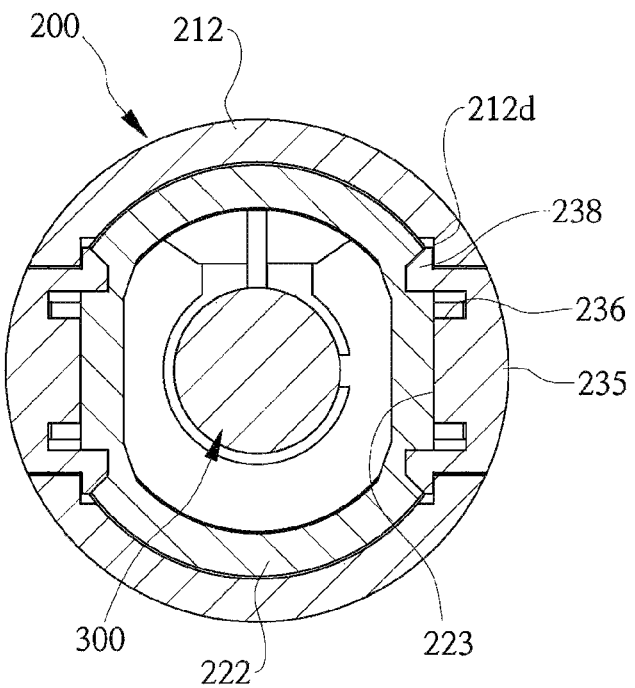
FIG. 12 is a schematic cross sectional view showing the extension member of the electrosurgical apparatus according to the second preferred embodiment of the present invention.

Referring to FIGS. 10 to 12, the electrosurgical apparatus according to the second preferred embodiment of the present invention is configured similar to the first embodiment except that the shape of a stopper 235 is different from the first embodiment. The extension member 200 includes the extension tube 210, the sliding tube 220, and the stopper 235. The extension tube 210 and the sliding tube 220 are similar to the first embodiment, and a detailed description thereof will be omitted.

The stopper 235 is detachably coupled to the through-coupling portion 212b, and to achieve this, a pair of elastic engaging hooks 238 are formed protruding from the middle portions of the opposite sides of the stopper 235, and a pair of engaging grooves 212d are formed in the opposite sides of the through-coupling portion 212b to be detachably engaged with the engaging hooks 238. Further, a blocking protrusion 236 is formed protruding from the center of the inner side of the stopper 235 facing the sliding tube 220. Herein, the blocking protrusion 236 is in surface contact with the flat portion 223, such that the guide protrusion 223a being moved forward along the guide rail 212a is stopped by the blocking protrusion 236. Here, since the blocking protrusion 236 is formed to have a large area, even though the practitioner moves the sliding tube 220 forward with more force than necessary, the guide protrusion 223a cannot pass over the blocking protrusion 236, and thus, the blocking protrusion 236 firmly supports the sliding tube 220 being inserted into the extension tube 210.

Figure 13:
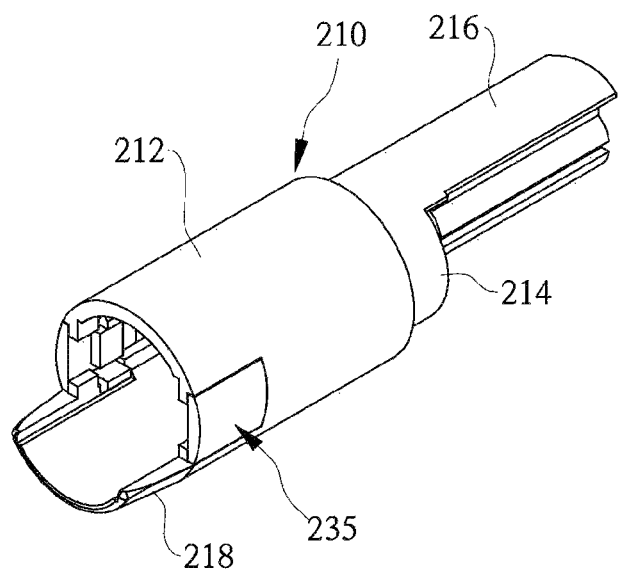
FIG. 13 is a view showing an extension tube provided in the extension member of the electrosurgical apparatus according to a third preferred embodiment of the present invention.
Figure 14:
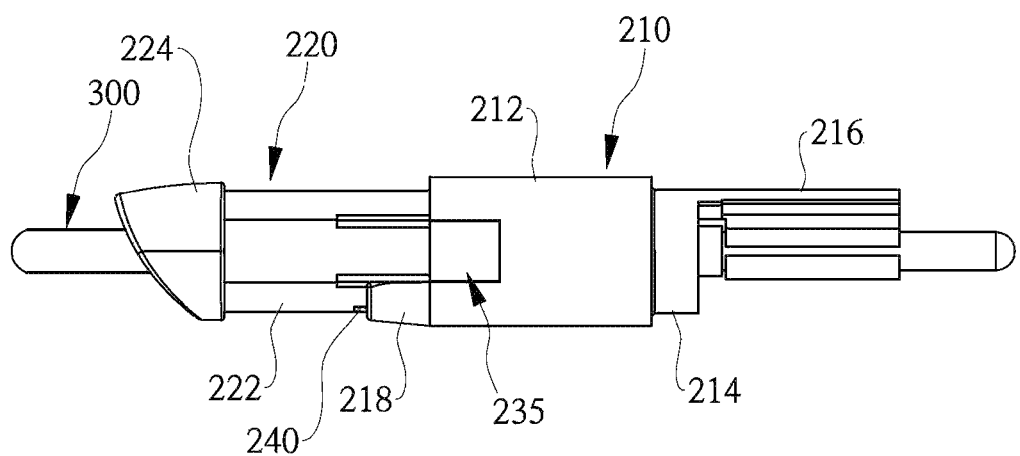
FIG. 14 is a view showing a state where a sliding tube of the electrosurgical apparatus according to the third preferred embodiment of the present invention is moved forward.

FIG. 13 is a view showing an extension tube provided in the extension member of the electrosurgical apparatus according to a third preferred embodiment of the present invention; and FIG. 14 is a view showing a state where a sliding tube of the electrosurgical apparatus according to the third preferred embodiment of the present invention is moved forward.

Figure 15:
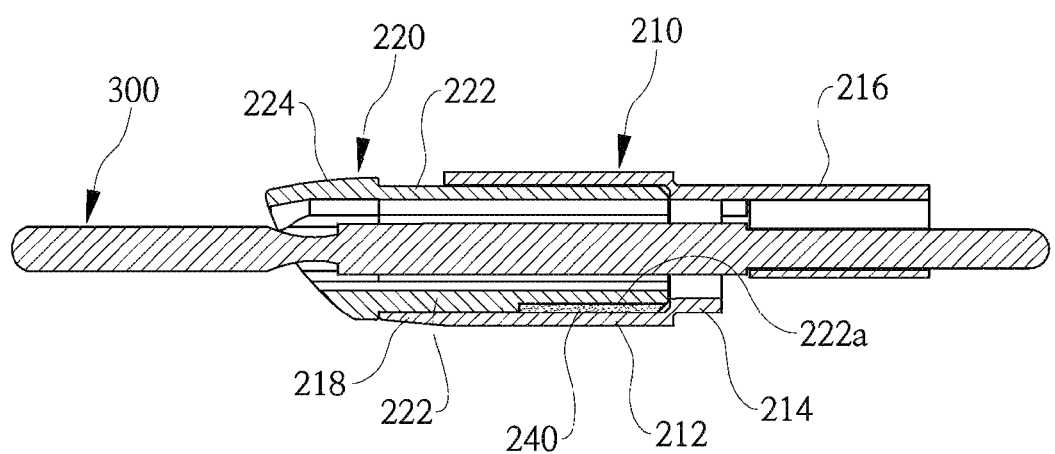
FIG. 15 is a view showing a friction part of the electrosurgical apparatus according to the third preferred embodiment of the present invention.

Referring to FIGS. 13 and 14, according to the electrosurgical apparatus 1000 according to the third preferred embodiment of the present invention shown in FIG. 13, the extension member 200 is further provided with a support protrusion 218, and a friction part 240 (shown in FIG. 15). The support protrusion 218 is formed protruding from the front lower portion of the extension tube 210 to support the lower portion of the sliding tube 220. The support protrusion 218 has a cross section formed in an arc shape, so as to support the lower portion of the outer circumferential surface of the insertion part 222 of the sliding tube 220 formed in a cylindrical shape. Thereby, the sliding tube 220 slides forward while being guided by the support protrusion 218.

Meanwhile, when the insertion part 222 of the sliding tube 220 inserted into the sliding guide part 212 of the extension tube 210 is moved forward, the insertion part 222 may be moved downward undesirably by gravity or may be shaken up and down. Thus, since the present invention is configured such that the support protrusion 218 firmly supports the lower portion of the sliding tube 220, even if the sliding tube 220 is moved forward, the sliding tube 220 is not shaken up and down undesirably.

FIG. 15 is a view showing a friction part of the electrosurgical apparatus according to the third preferred embodiment of the present invention.

Referring to FIG. 15, the friction part 240 of rubber material is provided between the sliding guide part 212 of the extension tube 210 and the insertion part 222 of the sliding tube 220. Here, the insertion part 222 of the sliding tube 220 is provided at the rear portion thereof with a friction guide groove 222a formed to be concave, such that the friction part 240 of rubber material or the like is disposed in the friction guide groove 222a.

The upper portion of the friction part 240 is brought in close contact with the friction guide groove 222a, and the lower portion of the friction part 240 is brought in close contact with the inner circumferential surface of the sliding guide part 212. Thereby, when the insertion part 222 is about to undesirably slide in the sliding guide part 212, the movement of the insertion part 222 in the advancing direction is obstructed by the friction part 240, so that the insertion part 222 cannot be undesirably moved but can slide only when there is pressure by a user.

Figure 16:
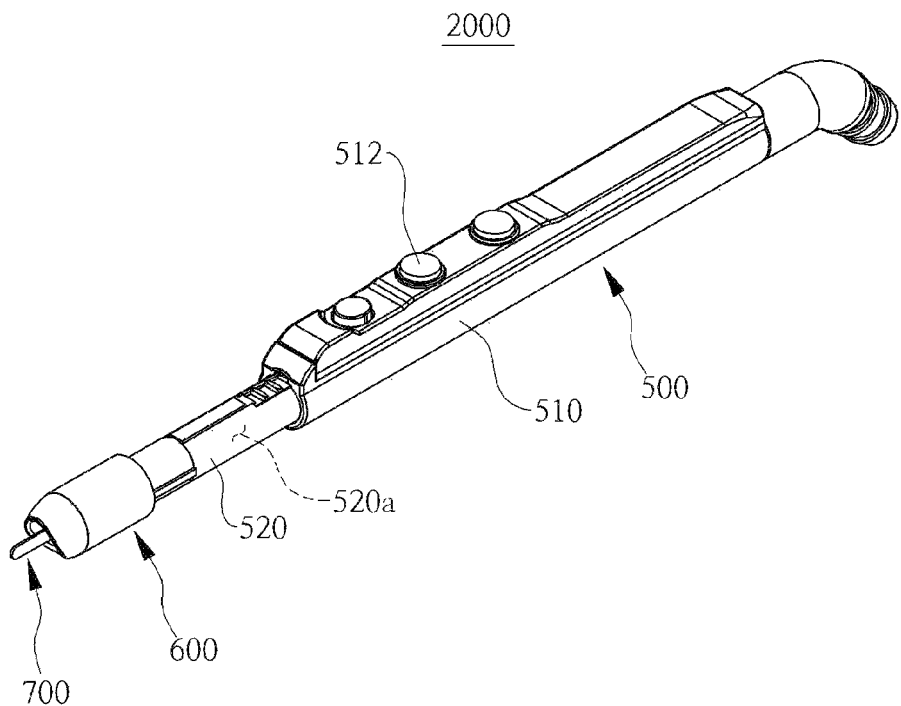
FIG. 16 is a schematic view showing an electrosurgical apparatus according to a fourth preferred embodiment of the present invention.
Figure 17:
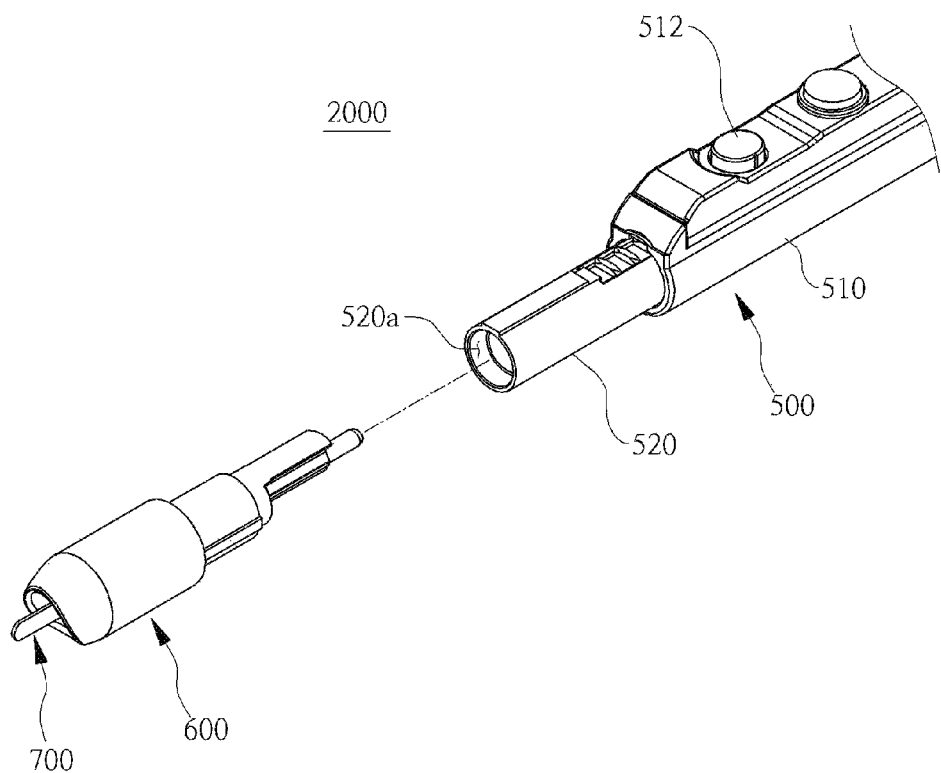
FIG. 17 is a view showing a state where an extension member of the electrosurgical apparatus according to the fourth preferred embodiment of the present invention is separated from a main body.

FIG. 16 is a schematic view showing an electrosurgical apparatus according to a fourth preferred embodiment of the present invention; and FIG. 17 is a view showing a state where an extension member of the electrosurgical apparatus according to the fourth preferred embodiment of the present invention is separated from a main body.

Referring to FIGS. 16 and 17, an electrosurgical apparatus 2000 according to the fourth preferred embodiment of the present invention is used by a practitioner such as a physician to cut or coagulate a part of a patient's body tissue, and includes a main body 500, an extension member 600, and a blade 700.

The main body 500 includes an outer body 510, and an inner body 520. The outer body 510 is formed in a long shape along the longitudinal direction so that the practitioner can grasp the same by hand, and a space (not shown) is formed therein along the longitudinal direction. Further, an operation button 512 is provided on the upper portion of the outer body 510, and a substrate (not shown) connected to the operation button 512 is provided inside the upper portion of the outer body 510. The substrate is configured to control the amount of high frequency energy transmitted from the outside by the operation of the operation button 512, and then transmit the adjusted amount to the blade 700. The current and voltage of high frequency may be varied depending on the patient's affected area and the surgical situation.

The inner body 520 is inserted into the lower portion of the outer body 510, and is formed in a long shape along the longitudinal direction, with a suction passage 520a formed therein along the longitudinal direction. The front of the suction passage 520a is coupled with the extension member 600, and the back thereof is connected with a separate suction means (not shown) provided outside to suck air, such that when the practitioner uses the blade 700 to cut or coagulate a part of the patient's body tissue, smoke spreading around the blade 700 is sucked in through the extension member 600 and the suction passage 520a. Meanwhile, although the main body 500 includes the outer body 510 and the inner body 520, this is only an embodiment of the present invention. In some cases, the inner body 520 may be omitted. In this case, the extension member 600 is coupled to the outer body 510.

The extension member 600 allows the entire length to be increased or decreased, thereby guiding a suction guider 630 (shown in FIG. 18), which will be described later, to be close to or away from the front end of the blade 700.

The blade 700 is used to cut or coagulate a part of the patient's body tissue using high frequencies during the surgical procedure, and is formed in a long shape along the longitudinal direction and is fastened to the extension member 600. Further, the blade 700 is disposed inside the extension member 600, with the front end thereof protruding outside through the suction guider 630, and the rear end thereof extending in the direction of the inner body 520. Here, the inner body 520 is provided therein with a contact guide (not shown) for connecting the substrate and the blade 700 to each other such that the blade 700 receives high frequencies from the main body 500.

Hereinafter, unless noted otherwise, the front, front side, or front end refers to the direction away from the main body 500, and the rear, rear side, or rear end refers to the direction close to the main body 500.

Figure 18:
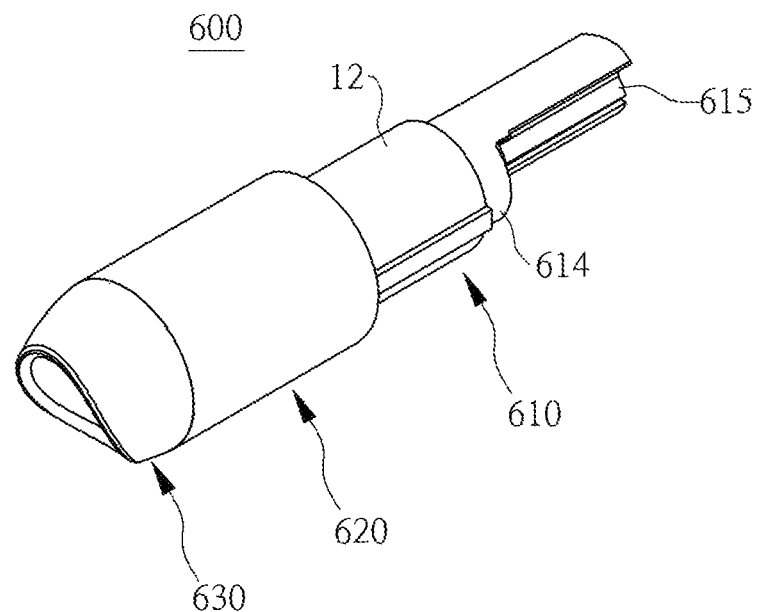
FIG. 18 is a view showing the extension member of the electrosurgical apparatus according to the fourth preferred embodiment of the present invention.
Figure 19:
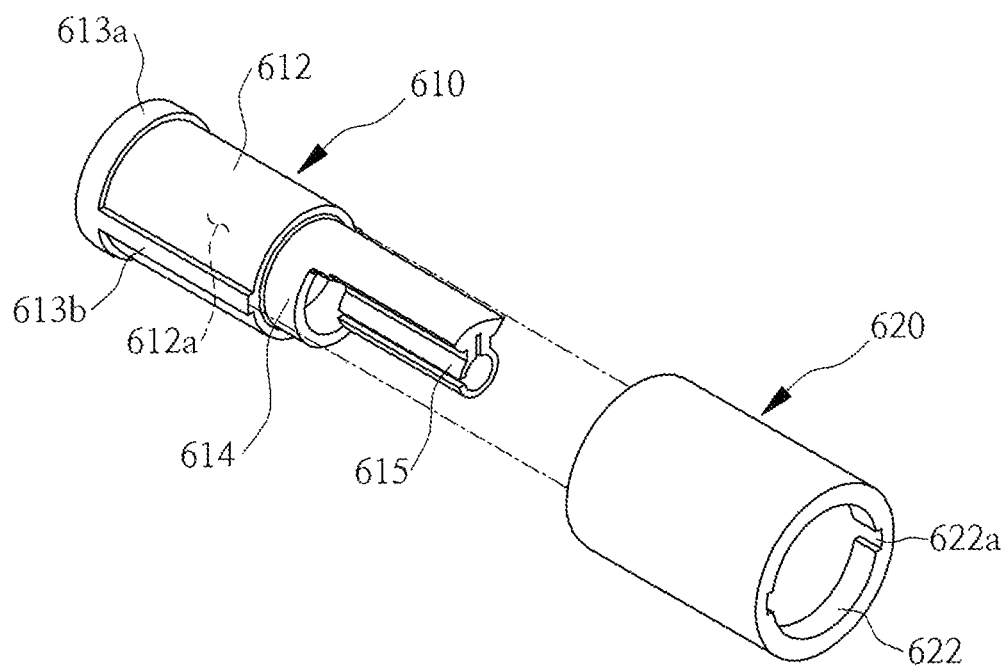
FIG. 19 is a schematic view showing a coupling process of an extension guide tube and a sliding part provided in the extension member of the electrosurgical apparatus according to the fourth preferred embodiment of the present invention.

FIG. 18 is a view showing the extension member of the electrosurgical apparatus according to the fourth preferred embodiment of the present invention; FIG. 19 is a schematic view showing a coupling process of an extension guide tube and a sliding part provided in the extension member of the electrosurgical apparatus according to the fourth preferred embodiment of the present invention; and FIG. 20 is a schematic sectional view of FIG. 19.

Figure 20:
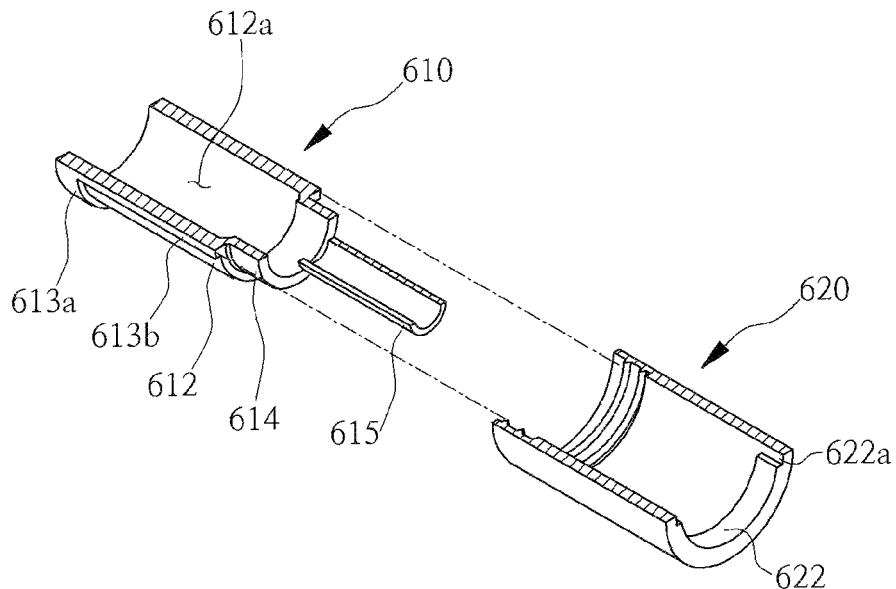
FIG. 20 is a schematic sectional view of FIG. 19.

Referring to FIGS. 18 to 20, the extension member 600 includes an extension guide tube 610, a sliding part 620, and the suction guider 630. As for the coupling process of the extension member 600, firstly, the sliding part 620 is coupled to the extension guide tube 610, and then the suction guider 630 is coupled to the sliding part 620. Hereinafter, a process of coupling the sliding part 620 to the extension guide tube 610 will be described.

The extension guide tube 610 includes: an extension part 612 formed in a tubular shape like a cylinder with an induction passage 612a formed therein; and an coupling part 614 protruding from a rear end of the extension part 612 facing the inner body 520 so as to be coupled with the inner body 520. Further, an outer circumferential surface of a front end of the extension part 612 disposed opposite to the main body 500 is protrudingly provided with a ring-shaped extension-locking step 613a, and the extension part 612 is protrudingly provided with at least one guide rail 613b on an outer side thereof along a longitudinal direction. The guide rail 613b may be provided with a pair of extension parts 612 at opposite sides thereof. Further, when the coupling part 614 is coupled to the inner body 520, the induction passage 612a of the extension part 612 and the suction passage 520a of the inner body 520 communicate with each other. The coupling part 614 is provided at a rear upper portion thereof with a fitting part 615 into which the blade 700 is inserted.

The sliding part 620 is formed in a tubular shape having an inner circumferential diameter larger than an outer circumferential diameter of the extension-locking step 613a, and may be formed of a transparent material so as to easily secure a visual field. The extension part 612 is inserted in the sliding part 620. Here, in the state where an open front end of the sliding part 620 is disposed at the outer circumferential surface of the extension part 612 via the coupling part 614, the sliding part is slidably moved forward or backward along the extension part 612. Here, along an inner circumferential surface of a rear end of the sliding part 620 disposed at a position facing the main body 500, a sliding-locking step 622 is formed protruding toward an outer circumferential surface of the extension part 612. Further, when the rear end of the sliding part 620 is disposed at the extension-locking step 613a while the sliding part 620 is slidably moved forwardly along the extension part 612, the sliding-locking step 622 is engaged with the extension-locking step 613a to limit forward movement of the sliding part 620. As such, since the sliding-locking step 622 is configured to be engaged with the extension-locking step 613a, the forwardly moving sliding part 620 is not undesirably separated from the extension part 612.

Further, the sliding-locking step 622 is concavely provided with a guide groove 622a to allow the guide rail 613b to be inserted thereinto, so that the guide groove 622a is moved along the guide rail 613b when the sliding part 620 slides. As such, since the sliding part 620 is slidably moved along the guide rail 613b, the sliding part 620 is not undesirably rotated within the extension part 612. This ensures that the upper portion and the lower portion of the suction guider 630, which will be described later, are not undesirably inverted, so that the upper portion of the suction guider 630 is protruded to be always away from the main body 500.

Further, since the guide groove 622a and the guide rail 613b are brought in contact with each other, a frictional force is generated between the guide groove 622a and the guide rail 613b. Thus, the sliding part 620 cannot be undesirably moved by the frictional force, so when the practitioner forcibly moves the sliding part 620 forward or backward while holding the sliding part, the sliding part 620 is maintained at a position moved by the practitioner.

Figure 21:
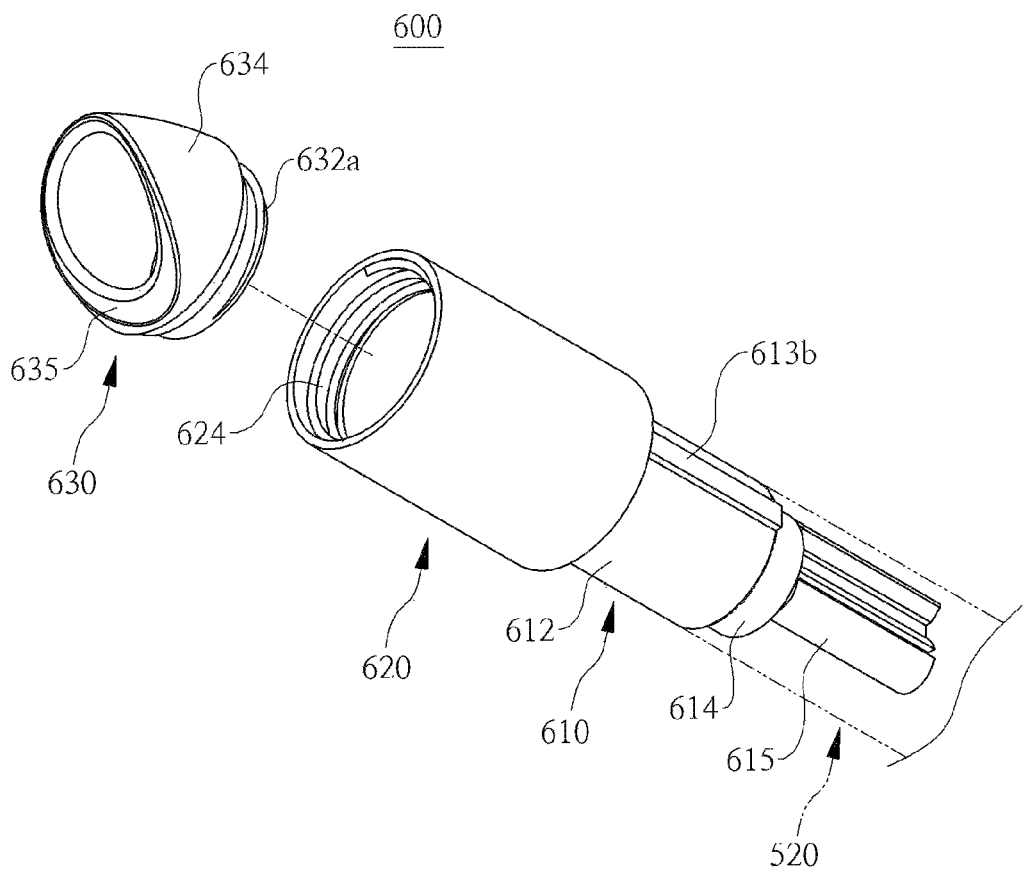
FIG. 21 is a schematic view showing a coupling process of a suction guider to the sliding part of the electrosurgical apparatus according to the fourth preferred embodiment of the present invention.
Figure 22:
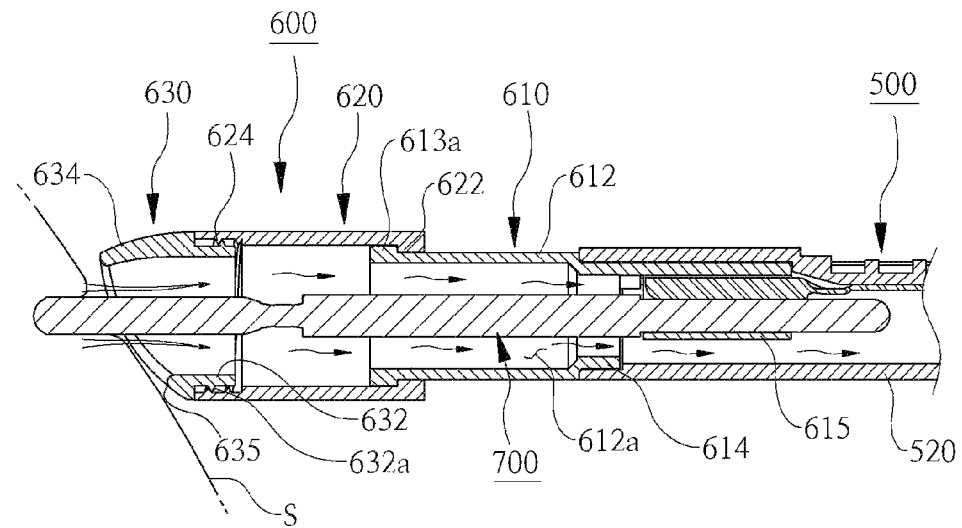
FIG. 22 is a sectional view showing an inclined portion provided in the suction guider of the electrosurgical apparatus according to the fourth preferred embodiment of the present invention.

FIG. 21 is a schematic view showing a coupling process of a suction guider to the sliding part of the electrosurgical apparatus according to the fourth preferred embodiment of the present invention; and FIG. 22 is a sectional view showing an inclined portion provided in the suction guider of the electrosurgical apparatus according to the fourth preferred embodiment of the present invention.

Referring to FIGS. 21 and 22, the suction guider 630 may be formed of a transparent material so as to easily secure a visual field, and includes: an inlet coupling part 632 coupled to the front end of the sliding part 620; and a suction induction part 634 integrally protruding from a front side of the inlet coupling part 632 to be away from the main body 500.

The inlet coupling part 632 is formed in a cylindrical shape. Further, an open front end of the sliding part 620 is disposed at the extension part 612 via the coupling part 614. Further, when the front end of the sliding part 620 is disposed to protrude forwardly more than the extension part 612, the inlet coupling part 632 is inserted in the front end of the sliding part 620. Here, the inlet coupling part 632 is formed with male threads 632a on the outer circumferential surface thereof, and the sliding part 620 is formed with female threads 624 on the inner circumferential surface of the front end thereof, and thus, the male threads 632a are engaged with the female threads 624. Further, the inner circumference of the inlet coupling part 632 is formed to be smaller than the outer circumference of the extension-locking step 613a, such that when the suction guider 630 coupled to the front end of the sliding part 620 is disposed at the extension-locking step 613a while the sliding part 620 is slidably moved backwardly along the extension part 612, the inlet coupling part 632 is engaged with the extension-locking step 613a to limit backward movement of the sliding part 620.

The suction induction part 634 is integrally protruding from a front side of the inlet coupling part 632. Here, the suction induction part 634 is configured to protrude to be gradually away from the main body 500 from a lower portion to an upper portion thereof, wherein the upper portion of the suction induction part 634 protrudes to be inclined downwardly so as to be close to the blade 700. Accordingly, with the practitioner gripping the outer body 510 at an angle of 45 degrees, the upper portion of the suction induction part 634 protrudes more toward the end of the blade 700 than the lower portion of the suction induction part 634. Thus, the smoke generated in the body tissue in contact with the end of the blade 700 is easily collected to the upper portion of the suction induction part 634.

Meanwhile, depending on the circumstances, the outer body 510 may be moved with the blade 700 deeply inserted into the skin. Here, a lower front end of the suction induction part 634 is moved along the skin while being brought in contact with the skin, wherein the suction induction part 634 is provided at the lower front end thereof with an inclined portion 635, so that the suction induction part is easily moved along the skin with the inclined portion 635 being stably brought in contact with the skin.

Figure 23:
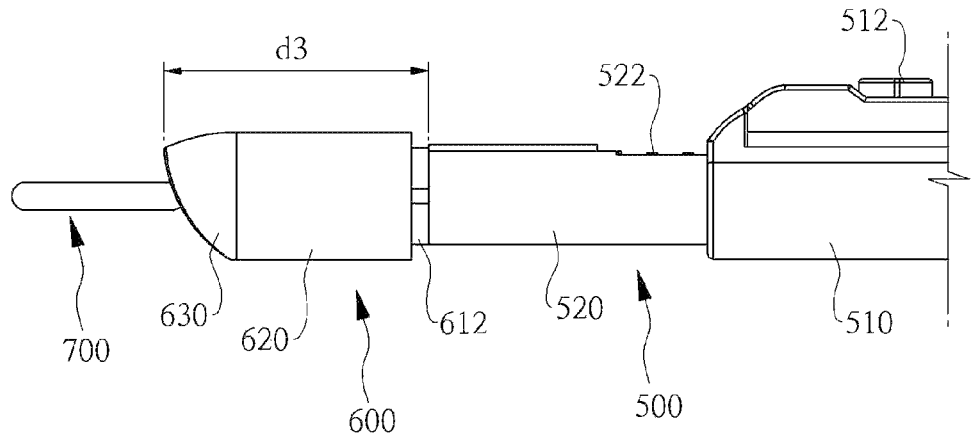
FIG. 23 is a view showing a state where the sliding part of the electrosurgical apparatus according to the fourth preferred embodiment of the present invention is moved backward.
Figure 24:
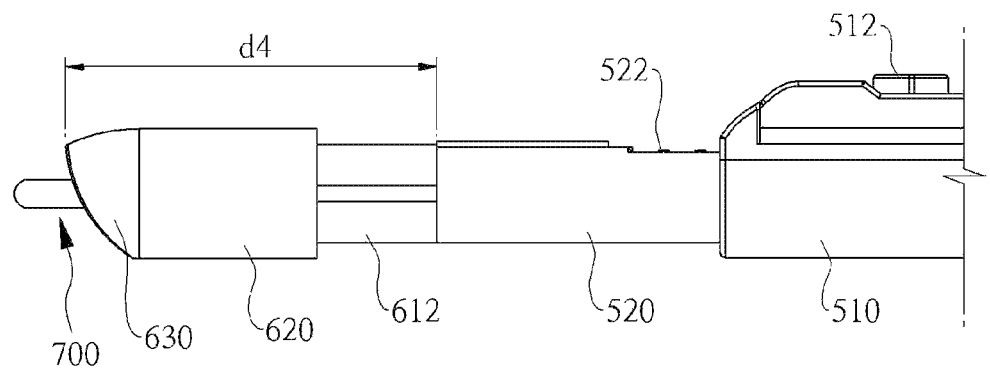
FIG. 24 is a view showing a state where the sliding part of the electrosurgical apparatus according to the fourth preferred embodiment of the present invention is moved forward.

FIG. 23 is a view showing a state where the sliding part of the electrosurgical apparatus according to the fourth preferred embodiment of the present invention is moved backward; and FIG. 24 is a view showing a state where the sliding part of the electrosurgical apparatus according to the fourth preferred embodiment of the present invention is moved forward.

Firstly, referring to FIG. 23, the sliding part 620 is in the state of being moved backward along the extension part 612, and here, a length d3 between the rear end of the extension part 612 and the front end of the suction induction part 634 is relatively short, and thus a large portion of the blade 700 is exposed outside the suction induction part.

Next, referring to FIG. 24, the sliding part 620 is in the state of being moved forward along the extension part 612, and here, a length d4 between the rear end of the extension part 612 and the front end of the suction induction part 634 is relatively long compared to FIG. 23. Here, a small portion of the blade 700 is exposed outside the suction induction part 634, so the end of the blade 700 and the suction induction part 634 are close to each other. Accordingly, when the sliding part 620 is moved forward as needed, the smoke generated in the body tissue in contact with the end of the blade 700 is easily collected to the inside of the suction induction part 634.

Figure 25:
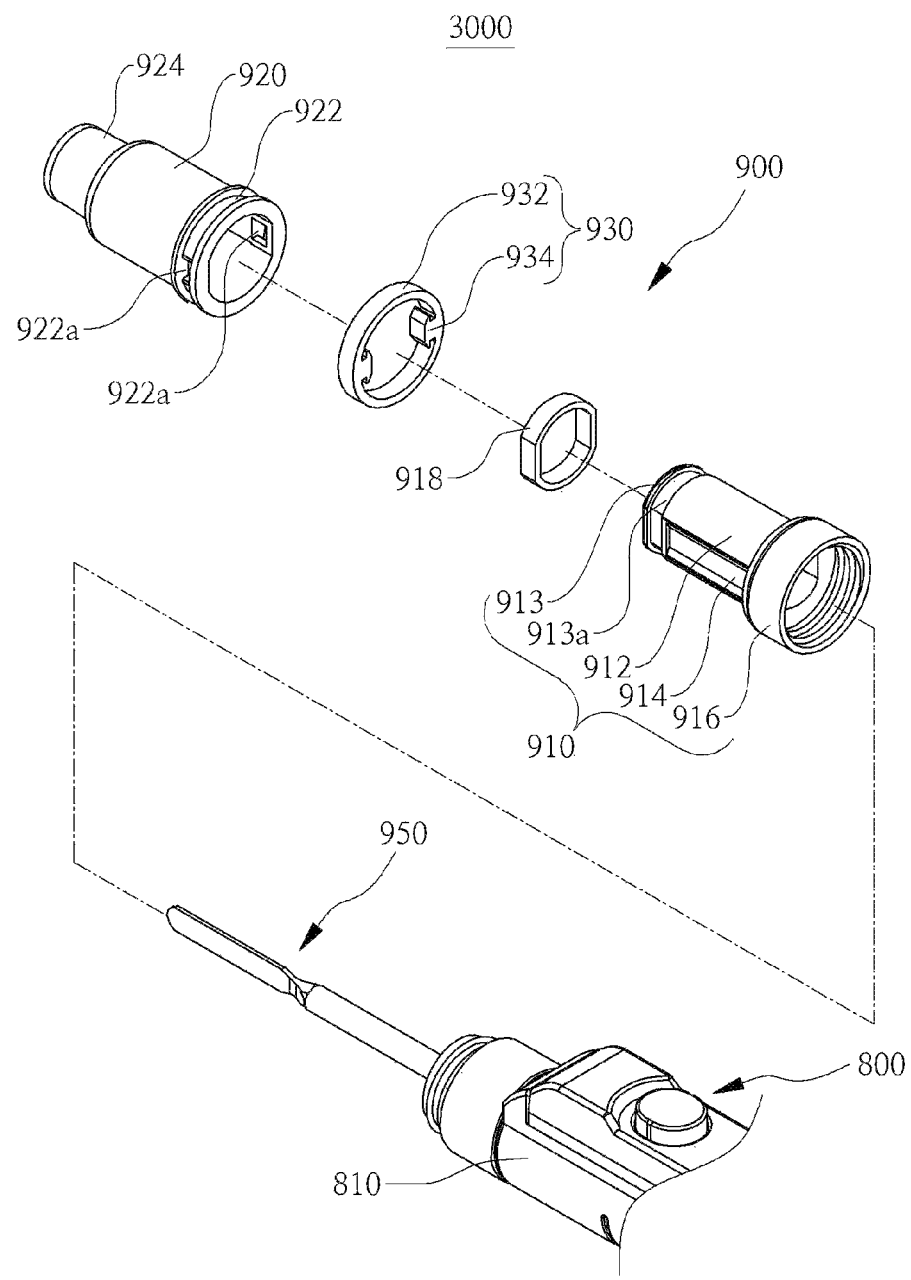
FIG. 25 is an exploded view showing an electrosurgical apparatus according to a fifth preferred embodiment of the present invention.

FIG. 25 is an exploded view showing an electrosurgical apparatus according to a fifth preferred embodiment of the present invention.

Referring to FIG. 25, an electrosurgical apparatus 3000 according to the fifth preferred embodiment of the present invention is used by a practitioner such as a physician to cut or coagulate a part of a patient's body tissue, and includes a main body 800, an extension member 900, and a blade 950.

The main body 800 includes: an outer body 810 extending in a longitudinal direction, and being formed therein with a space (not shown) along the longitudinal direction; and an inner body 820 configured to be slidable along the space, and provided therein with the suction passage 820a along the longitudinal direction. The main body 800 is similar to the main body 500 shown in FIG. 16, and a detailed description thereof will be omitted.

The extension member 900 allows the entire length to be increased or decreased, thereby guiding an induction extension part 924, which will be described later, to be close to or away from the front end of the blade 950.

The blade 950 is used to cut or coagulate a part of the patient's body tissue using high frequencies during the surgical procedure, is formed in a long shape along the longitudinal direction, and is configured such that a first end thereof is fixed to the inner body 820 and a second end thereof is exposed outside via the extension member 900. The inner body 820 is provided therein with a power connection part 822 (shown in FIG. 26) to be electrically connected to the blade 950, so the blade 950 receives high frequencies from the main body 800.

Hereinafter, unless noted otherwise, the front, front side, or front end refers to the direction away from the main body 800, and the rear, rear side, or rear end refers to the direction close to the main body 800.

Figure 26:
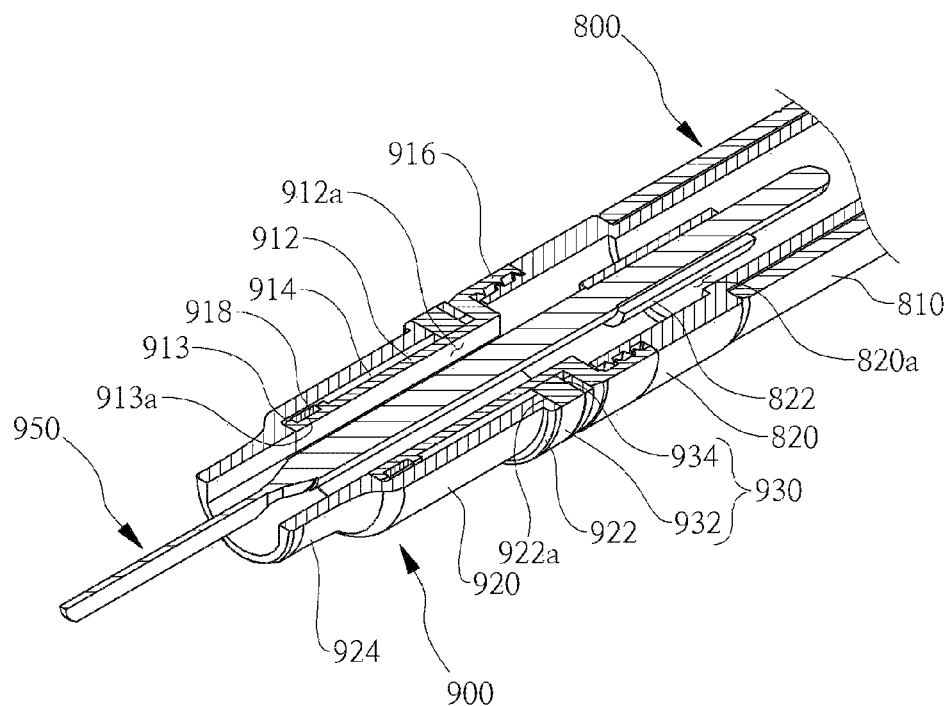
FIG. 26 is a longitudinal sectional view showing the electrosurgical apparatus according to the fifth preferred embodiment of the present invention.
Figure 27:
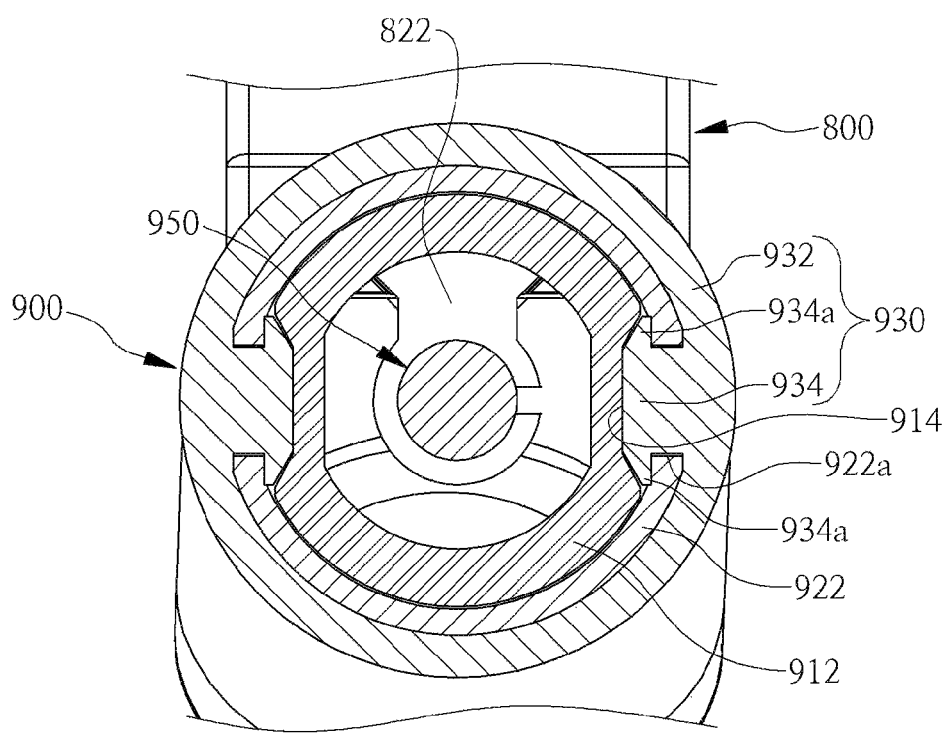
FIG. 27 is a cross sectional view showing the electrosurgical apparatus according to the fifth preferred embodiment of the present invention.

FIG. 26 is a longitudinal sectional view showing the electrosurgical apparatus according to the fifth preferred embodiment of the present invention; and FIG. 27 is a cross sectional view showing the electrosurgical apparatus according to the fifth preferred embodiment of the present invention.

Referring to FIGS. 25 to 27, the extension member 900 includes a length adjusting tube 910 coupled to the main body 800, a sliding part 920 into which the length adjusting tube 910 is inserted, and a stopper 930.

The length adjusting tube 910 includes: a length adjusting part 912 formed in a cylindrical tubular shape, and formed with an induction passage 912a therein to communicate with the suction passage 820a; a coupling part 916 protruding from a rear end of the length adjusting part 912 facing the inner body 820 so as to be coupled with the main body 800; and a length adjusting-locking step 913 protruding from an outer circumferential surface of a front end of the length adjusting part 912 disposed opposite to the main body 800.

The outer circumferential surface of the length adjusting-locking step 913 is formed with a fitting groove 913a to allow an O-ring 918 to be fitted thereover. The O-ring 918 is made of an elastic material such as rubber having a large frictional force, and the outer circumferential surface of the O-ring 918 is brought in close contact with the inner circumferential surface of the sliding part 920, thereby preventing the sliding part 920 from being undesirably moved.

The sliding part 920 is formed in a tubular shape having an inner circumferential diameter larger than an outer circumferential diameter of the length adjusting-locking step 913. After the length adjusting part 912 is inserted in the sliding part 920, the sliding part 920 slides while being guided by the length adjusting part 912. Further, the sliding part 920 is formed to have a length similar to a length of the length adjusting part 912, such that in the state where the rear end of the sliding part 920 being moved along the length adjusting part 912 is positioned to be in contact with the coupling part 916, the front end of the sliding part 920 does not protrude more than the front end of the length adjusting part 912. Here, the front end of the sliding part 920 is integrally provided with the induction extension part 924 protruding forwardly more than the front end of the length adjusting part 912. The induction extension part 924 is configured to have a diameter smaller than a diameter of the sliding part 920. Further, the blade 950 protrudes outside the induction extension part 924 via the sliding part 920. The sliding part 920 and the induction extension part 924 may be formed of a transparent material so as to easily secure a visual field.

The stopper 930 is disposed at the rear end of the sliding part 920 facing the main body 800, and to achieve this, the outer circumferential surface of the rear end of the sliding part 920 is concavely formed with an insertion guide groove 922, and through-holes 922a are formed through the insertion guide groove 922 at opposite sides thereof. Further, the stopper 930 includes: a ring-shaped fitting part 932 fitted over the insertion guide groove 922; and a stop protrusion 934 protruding from the fitting part 932 toward inside the sliding part 920 via the through-hole 922a. Further, the stop protrusion 934 is provided with a pair of latching portions 934a protruding from opposite sides of a front end portion thereof. The stopper 930 is made of elastic material such as rubber or silicone, so that when the front end portion of the stop protrusion 934 is inserted into the through-hole 922a, the pair of latching portions 934a are elastically deformed and then are engaged with an inner side of the sliding part 920. Further, in the process of inserting the front end of the length adjusting part 912 into the rear end of the sliding part 920 to which the stopper 930 is coupled, when the length adjusting-locking step 913 forcibly passes by the stop protrusion 934 of the stopper 930, the stop protrusion 934 is elastically deformed by pressure of the length adjusting-locking step 913.

Further, when the sliding part 920 and the length adjusting part 912 are coupled to each other as the length adjusting-locking step 913 forcibly passes by the stop protrusion 934 of the stopper 930, the sliding part 920 slides forward and backward along the length adjusting part 912, wherein when the rear end of the sliding part 920 is moved toward the front end of the length adjusting part 912, the stop protrusion 934 is engaged with the length adjusting-locking step 913, and thus, the sliding part 920 is not undesirably separated from the length adjusting part 912.

Meanwhile, the length adjusting part 912 is provided with a guide groove 914 concavely formed from the front end towards the rear end thereof, and after the front end of the length adjusting part 912 is inserted into the rear end of the sliding part 920, when the sliding part 920 is moved along the length adjusting part 912, the stop protrusion 934 of the stopper 930 slides along the guide groove 914, whereby the sliding part 920 cannot be undesirably rotated, and thus, when a user arbitrarily moves the sliding part 920 while gripping the sliding part 920, it is possible to stably move the sliding part 920.

Figure 28:
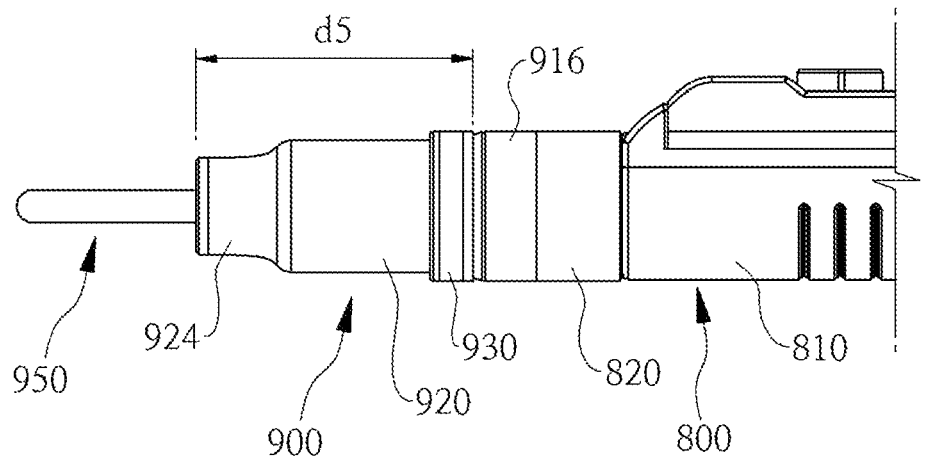
FIG. 28 is a view showing a state where a sliding part of the electrosurgical apparatus according to the fifth preferred embodiment of the present invention is moved backward.
Figure 29:
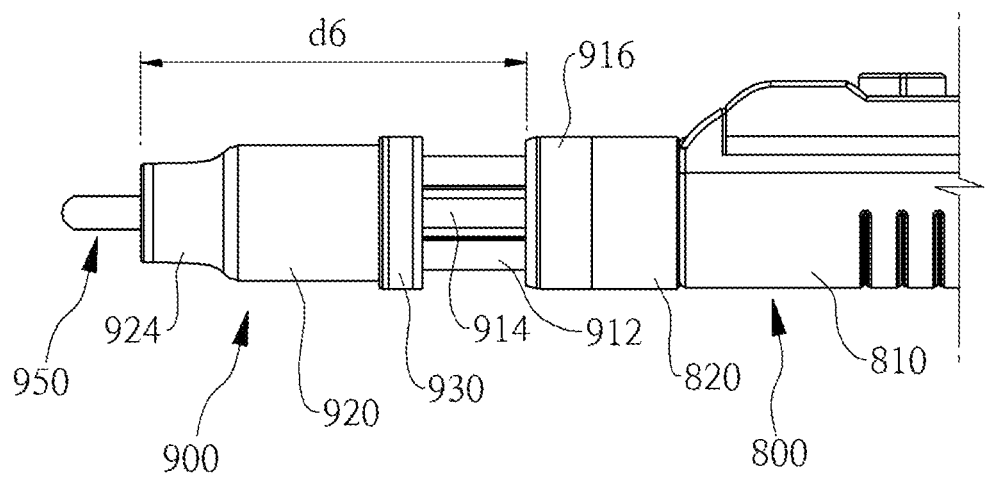
FIG. 29 is a view showing a state where the sliding part of the electrosurgical apparatus according to the fifth preferred embodiment of the present invention is moved forward.

FIG. 28 is a view showing a state where a sliding part of the electrosurgical apparatus according to the fifth preferred embodiment of the present invention is moved backward; FIG. 29 is a view showing a state where the sliding part of the electrosurgical apparatus according to the fifth preferred embodiment of the present invention is moved forward; and FIG. 30 is a sectional view of FIG. 29.

Firstly, referring to FIG. 28, the sliding part 920 is in the state of being moved backward along the length adjusting part 912, and here, a length d5 between the rear end of the length adjusting part 912 and the front end of the induction extension part 924 is relatively short, and thus a large portion of the blade 950 is exposed outside the induction extension part 924.

Figure 30:
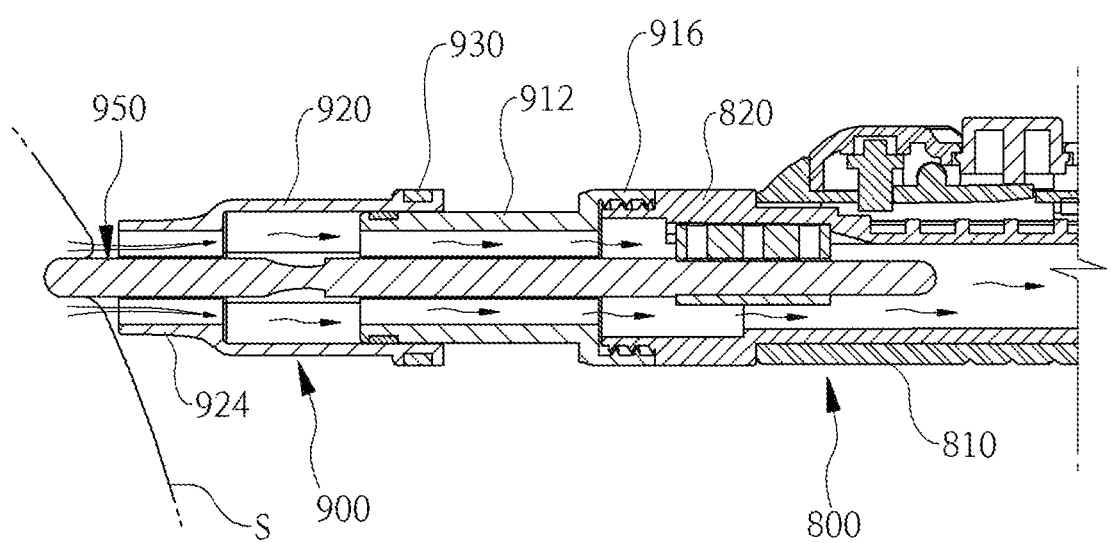
FIG. 30 is a sectional view of FIG. 29.

Next, referring to FIGS. 29 and 30, the sliding part 920 is in the state of being moved forward along the length adjusting part 912, and here, a length d6 between the rear end of the length adjusting part 912 and the front end of the induction extension part 924 is relatively long compared to FIG. 28. Here, a small portion of the blade 950 is exposed outside the induction extension part 924, so the end of the blade 950 and the induction extension part 924 are close to each other. Accordingly, when the sliding part 920 is moved forward as needed, the smoke generated in the body S in contact with the end of the blade 950 is easily collected to the inside of the induction extension part 924.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An electrosurgical apparatus comprising:
   a main body formed with a suction passage therein;
   an extension member including a length adjusting tube coupled to a side of the main body and formed therein with an induction passage communicating with the suction passage, and a sliding part configured to slide while being guided by the length adjusting tube; and
   a blade configured such that a first end thereof protrudes outside through the sliding part, and a second end thereof extends to be electrically connected to the main body and receives high frequencies from the main body,
   wherein an entire length of the extension member is adjusted according to a position of the sliding part sliding along the length adjusting tube,
   wherein the length adjusting tube includes:
      a length adjusting part formed in a tubular shape, and formed with the induction passage therein;
      a coupling part protruding from a rear end of the length adjusting part facing the main body so as to be coupled with the main body; and
      a length adjusting-locking step protruding from an outer circumferential surface of a front end of the length adjusting part disposed opposite to the main body,
   wherein the sliding part includes a stopper having elasticity protruding inwardly from a rear end thereof facing the main body,
   wherein, in a process of inserting the front end of the length adjusting part into the rear end of the sliding part, the stopper is elastically deformed by pressure of the length adjusting-locking step when the length adjusting-locking step passes by the stopper,
   wherein the length adjusting part is provided with a guide groove concavely formed from the front end towards the rear end thereof,
   wherein, after the front end of the length adjusting part is inserted into the rear end of the sliding part, when the sliding part is moved along the length adjusting part, the stopper slides along the guide groove,
   wherein the sliding part has a tubular shape having an inner circumferential diameter larger than an outer circumferential diameter of the length adjusting-locking step,
   wherein the sliding part is provided with a first through-hole and a second through-hole, which are positioned at the rear end of the sliding part, and
   wherein the stopper includes:
      a ring-shaped fitting part fitted over an outer circumferential surface of the rear end of the sliding part; and
      a first stop protrusion protruding from the fitting part toward inside the sliding part via the first through-hole; and
      a second stop protrusion protruding from the fitting part toward inside the sliding part via the second through-hole, and
   wherein each of the first stop protrusion and the second stop protrusion is a T-shaped latch having a head configured to be elastically deformed to correspond to a shape of the guide groove and configured to be engaged with an inner side of the sliding part.

2. The electrosurgical apparatus of claim 1, wherein the length adjusting-locking step is provided with a fitting groove to allow an O-ring to be fitted over the outer circumferential surface thereof, and
   an outer circumferential surface of the O-ring is brought in close contact with an inner circumferential surface of the sliding part.

3. The electrosurgical apparatus of claim 1, wherein, in a state where the rear end of the sliding part being moved along the length adjusting part is positioned to be in contact with the coupling part, the sliding part is integrally provided at a front end thereof with an induction extension part protruding forwardly more than the front end of the length adjusting part,
   the induction extension part is configured to have a diameter smaller than a diameter of the sliding part, and
   the blade protrudes outside the induction extension part via the sliding part.

4. The electrosurgical apparatus of claim 1, wherein the main body includes:
   an outer body extending in a longitudinal direction, and being formed therein with a space along the longitudinal direction; and
   an inner body configured to be slidable along the space, and provided therein with the suction passage along the longitudinal direction,
   wherein the length adjusting tube is coupled to the inner body.

5. An electrosurgical apparatus comprising: a main body formed with a suction passage therein; an extension member including an extension tube coupled to a side of the main body and formed therein with an induction passage communicating with the suction passage, and a sliding tube configured to slide along the extension tube while being inserted in the extension tube, wherein an open front end of the sliding tube has an inclined shape such that the open front end protrudes to be gradually away from the main body from a bottom of the open front end to a top of the open front end; and a blade having a first side that protrudes outside through the inclined shape of the open front end of the sliding tube, and a second side that is electrically connected to the main body to receive high frequencies from the main body, wherein an entire length of the extension member is adjusted according to a position of the sliding tube sliding along the extension tube, wherein the extension tube includes: a sliding guide part formed in a tubular shape; an insertion guide part formed integrally protruding from a rear end of the sliding guide part facing the main body to be coupled to the main body; the induction passage formed through the sliding tube and the insertion guide part; and a coupling part configured to allow the blade to be coupled to the sliding guide part or the insertion guide part, wherein the sliding tube includes: an insertion part configured to slide while being inserted into the sliding guide part; and a grip part integrally provided at a front end of the insertion part, wherein an open front end of the grip part is provided with a suction guider that corresponds to the open front end of the sliding tube, wherein the sliding guide part is provided an inner circumferential surface thereof with a guide rail concavely formed along a longitudinal direction of the sliding guide part, with the guide rail provided with a through-coupling portion at an end thereof disposed opposite to the main body to be exposed to an outside, wherein the insertion part is provided an outer circumferential surface thereof with a guide protrusion to slide along the guide rail, and wherein, when the insertion part is inserted into the sliding guide part, the guide protrusion is inserted into the guide rail through the through-coupling portion.

6. The electrosurgical apparatus of claim 5, wherein an upper portion of the suction guider is formed to be inclined downward to be close to the blade.

7. The electro surgical apparatus of claim 5, wherein the grip part is formed to have an outer circumferential diameter larger than an outer circumferential diameter of the insertion part.

8. The electrosurgical apparatus of claim 5, wherein a stopper is detachably coupled to the through-coupling portion, with a blocking protrusion formed protruding from an inner side of the stopper,
when the stopper is detached from the through-coupling portion, the end of the guide rail is exposed to the outside, such that the guide protrusion is inserted into the guide rail, and
when the stopper is coupled to the through-coupling portion in a state where the guide protrusion is inserted into the guide rail, the end of the guide rail is blocked from the outside by the blocking protrusion, such that the guide protrusion being moved along the guide rail is stopped by the blocking protrusion.

9. The electrosurgical apparatus of claim 8, wherein the blocking protrusion protrudes from a middle portion of the stopper.

10. The electrosurgical apparatus of claim 8, wherein the insertion part is provided with a flat portion at a position of the outer circumferential surface thereof facing the guide rail, and
when the insertion part is moved along the sliding guide part, the flat portion slides in contact with the blocking protrusion.

11. The electrosurgical apparatus of claim 8, wherein the stopper is provided with elastic engaging hooks on opposite sides thereof, and the through-coupling portion is provided with engaging grooves on opposite sides thereof to be engaged with the engaging hooks when the stopper is coupled through the through-coupling portion.

12. The electrosurgical apparatus of claim 11, wherein the insertion part is provided with hook guide channels formed to be concave at positions of opposite sides thereof brought in contact with the engaging hooks such that the engaging hooks slide while being guided thereby.

13. The electrosurgical apparatus of claim 5, wherein the main body includes:
an outer body formed with a space therein; and
an inner body configured to be slidable along the space, and provided with the suction passage therein,
wherein the extension tube is coupled to the inner body.

14. The electrosurgical apparatus of claim 5, wherein the extension tube is provided with a support protrusion at a lower side portion thereof to support a lower portion of the sliding tube.

15. The electrosurgical apparatus of claim 5, wherein a friction part is provided between the extension tube and the sliding tube, and
a first side of the friction part is brought into close contact with the sliding tube, and a second side of the friction part is brought into close contact with the extension tube.

16. The electrosurgical apparatus of claim 15, wherein the sliding tube is provided with a friction guide groove formed to be concave to guide the friction part.

17. An electrosurgical apparatus comprising: a main body formed with a suction passage therein; an extension member including an extension guide tube coupled to a side of the main body and formed therein with an induction passage communicating with the suction passage, a sliding part configured to slide along the extension guide tube, and a suction guider coupled to a front end of the sliding part that does not face the main body, wherein an open front end of the suction guider has an inclined shape such that the open front end protrudes to be gradually away from the main body from a bottom of the suction guider to a top of the suction guider; and a blade locked to an inside of the extension guide tube, and having a first side that protrudes outside through the inclined shape of the open front end of the suction guider, and a second side that is connected to the main body to receive high frequencies from the main body, wherein an open rear end of the suction guider is coupled to the front end of the sliding part, wherein the extension guide tube includes an extension part formed in a tubular shape with the induction passage formed therein, a coupling part protruding from a rear end of the extension part facing the main body so as to be coupled with the main body, and an extension-locking step protruding from an outer circumferential surface of a front end of the extension part disposed opposite to the main body, and wherein the sliding part is formed in a tubular shape having an inner circumferential diameter larger than an outer circumferential diameter of the extension-locking step, and includes a sliding-locking step protruding toward an outer circumferential surface of the extension part along an inner circumferential surface of a rear end of the sliding part disposed at a position facing the main body.

18. The electrosurgical apparatus of claim 17, wherein the suction guider is configured to have an inner circumference smaller than an outer circumference of the extension-locking step,
- when the rear end of the sliding part is disposed at the extension-locking step while the sliding part is slidably moved forwardly along the extension part, the sliding-locking step is engaged with the extension-locking step to limit forward movement of the sliding part, and
- when the suction guider coupled to the front end of the sliding part is disposed at the extension-locking step while the sliding part is slidably moved backwardly along the extension part, the suction guider is engaged with the extension-locking step to limit backward movement of the sliding part.

19. The electrosurgical apparatus of claim 17, wherein the extension part is protrudingly provided with at least one guide rail on an outer side thereof along a longitudinal direction,
- the sliding-locking step is concavely provided with a guide groove to allow the guide rail to be inserted thereinto, and
- the guide groove is moved along the guide rail when the sliding part slides.

20. The electrosurgical apparatus of claim 19, wherein the guide groove and the guide rail are brought in contact with each other, and the guide groove is moved along the guide rail by external pressure.

21. The electrosurgical apparatus of claim 17, wherein the suction guider includes: an inlet coupling part coupled to the front end of the sliding part; and a suction induction part integrally protruding from a front side of the inlet that corresponds to the open front end of the suction guider, wherein an upper portion of the suction induction part protrudes to be inclined so as to be close to the blade.

22. The electrosurgical apparatus of claim 17, wherein the suction guider includes: an inlet coupling part coupled to the front end of the sliding part; and a suction induction part integrally protruding from a front side of the inlet that corresponds to the open front end of the suction guider,
- wherein the suction induction part is provided at a lower end thereof with an inclined portion to be inclined.

23. The electrosurgical apparatus of claim 17, wherein the main body includes:
- an outer body extending in a longitudinal direction, and being formed therein with a space along the longitudinal direction; and
- an inner body configured to be slidable along the space, and provided therein with the suction passage along the longitudinal direction,
- wherein the extension guide tube is coupled to the inner body.

* * * * *